(12) United States Patent
Li et al.

(10) Patent No.: US 12,196,739 B2
(45) Date of Patent: Jan. 14, 2025

(54) ROCK PHYSICO-MECHANICAL TESTING CHAMBER AND THREE-DIMENSIONAL MULTI-FIELD INFORMATION PERCEPTION CABIN IN SIMULATED ENVIRONMENTS OF DEEP EARTH, DEEP SPACE, AND DEEP SEA

(71) Applicant: SHENZHEN UNIVERSITY, Shenzhen (CN)

(72) Inventors: Minghui Li, Shenzhen (CN); Heping Xie, Shenzhen (CN); Hongwei Zhou, Shenzhen (CN); Cunbao Li, Shenzhen (CN); Mingzhong Gao, Shenzhen (CN); Jun Lu, Shenzhen (CN); Cancan Chen, Shenzhen (CN); Zhouqian Wu, Shenzhen (CN); Delei Shang, Shenzhen (CN)

(73) Assignee: SHENZHEN UNIVERSITY, Shenzhen (CN)

( * ) Notice: Subject to any disclaimer, the term of this patent is extended or adjusted under 35 U.S.C. 154(b) by 0 days.

(21) Appl. No.: 18/588,115

(22) Filed: Feb. 27, 2024

(65) Prior Publication Data
US 2024/0295541 A1 Sep. 5, 2024

(30) Foreign Application Priority Data
Mar. 2, 2023 (CN) .......................... 202310192101.2

(51) Int. Cl.
*G01N 33/24* (2006.01)
(52) U.S. Cl.
CPC .................... *G01N 33/24* (2013.01)

(58) Field of Classification Search
CPC ...................................................... G01N 33/24
See application file for complete search history.

(56) References Cited

U.S. PATENT DOCUMENTS 11,761,865 B2 * 9/2023 Liu .......................... G01N 3/12
73/788
2019/0033198 A1 1/2019 Atapour

FOREIGN PATENT DOCUMENTS

| CN | 104655495 A | * | 5/2015 |
| CN | 109828155 A | | 5/2019 |

(Continued)

OTHER PUBLICATIONS

Machine Translation of CN-111175468-A (Year: 2020).*
(Continued)

*Primary Examiner* — Nguyen Q. Ha
(74) *Attorney, Agent, or Firm* — Jeenam Park

(57) ABSTRACT

The present invention relates to a rock physico-mechanical testing chamber and a three-dimensional multi-field information perception cabin in simulated environments of deep earth, deep space, and deep sea. The testing chamber comprises a cabin body and 6 butting indenters; the 6 butting indenters are pairwise located in an X-axis direction, a Y-axis direction and a Z-axis direction; the 6 butting indenters are respectively mounted in through holes on six faces of the cabin body, inner ends of the butting indenters extend into the cabin body, outer ends of the butting indenters are exposed out of the cabin body, and the butting indenters can axially move relative to the cabin body. The present application can be used to achieve the reservoir rock mechanical behavior testing in real time under high and low environments.

7 Claims, 23 Drawing Sheets

(56) References Cited

FOREIGN PATENT DOCUMENTS

| | | | | |
|---|---|---|---|---|
| CN | 110426286 | A | 11/2019 | |
| CN | 110595909 | A | 12/2019 | |
| CN | 111175468 | A * | 5/2020 | ........... G01N 33/222 |
| CN | 111426575 | A | 7/2020 | |
| CN | 111707538 | A | 9/2020 | |
| CN | 111965091 | A | 11/2020 | |
| CN | 113552323 | A * | 10/2021 | ............. G01N 33/24 |
| CN | 113686693 | A | 11/2021 | |
| KR | 101683619 | B1 | 12/2016 | |

OTHER PUBLICATIONS

Machine Translation of CN-104655495-A (Year: 2015).*
Machine Translation of CN-113552323-A (Year: 2021).*
Chen Cancan et al. "Experimental study of stress relaxation characteristics of sandstone under stress and pore-water pressure coupling" vol. 41, Issue 6, Jun. 30, 2022 (Jun. 30, 2022), pp. 1193-1207.
Jiang Xu et al. "Experimental study of generalized stress relaxation of rock based on 3D-DIC technology" «Rock and Soil Mechanics», vol. 42, Dec. 31, 2021(Dec. 31, 2021), pp. 27-38.

* cited by examiner

ROCK PHYSICO-MECHANICAL TESTING CHAMBER AND THREE-DIMENSIONAL MULTI-FIELD INFORMATION PERCEPTION CABIN IN SIMULATED ENVIRONMENTS OF DEEP EARTH, DEEP SPACE, AND DEEP SEA

BACKGROUND

1. Technical Field

The present invention relates to the technical field of rock mechanical behavior testing, and in particular, to a rock physico-mechanical testing chamber and a three-dimensional multi-field information perception cabin in simulated environments of deep earth, deep space, and deep sea.

2. Description of Related Art

China is in the stage of accelerating industrialization and urbanization, and the demand for resources is increasing day by day. The resources in the shallow parts of the earth have gradually been depleted. The deep earth, deep space and deep sea areas contain a large amount of resources and energy, and therefore, the demand for resources and energy is gradually shifting to the deep at present. Due to the unknown and lack of scientific theories in the deep earth, deep space and deep sea areas, the implementation of related projects faces huge challenges. For the extraction and utilization of deep earth resources, an extraction environment faces "high stress, high ground temperature, high osmotic pressure" and more severe engineering disturbances, which makes the development of deep resources difficult and costly. Moreover, the disaster accidents are high in frequency, large in magnitude, and difficult to predict, which seriously affects the safe and efficient extraction of deep resources. Therefore, the development of related deep rock physico-mechanical tests has great theoretical, engineering and strategic significance. At present, relevant theories and technologies for the exploration and development of conventional resources in the shallow part of the earth crust are mature; however, theories and technologies for the development and utilization of deep earth, deep space and deep sea resources are lacked, and establishment of theories and technical systems is inseparable from a matched physico-mechanical experiment system.

For the projects of mining of deep mineral resources, geological storage of carbon dioxide, underground space development and geothermal development, the stress environment is a true triaxial stress state due to the effects of tectonic stress, mining disturbance, occurrence environment, formation stress, reservoir water environment and the like, and particularly after the deep areas are reached, the stress has the characteristic of high pressure.

In the conventional technology, the in-situ environments of deep earth, deep space and deep sea cannot be simulated, and multi-field and multi-parameter real-time testing of rocks in an in-situ multi-field coupling environment cannot be performed, resulting in distortion of experimental data.

SUMMARY

To resolve the foregoing technical problem, the present application provides a rock physico-mechanical testing chamber and a three-dimensional multi-field information perception cabin in simulated environments of deep earth, deep space, and deep sea.

The present application is implemented by the following technical solutions.

The rock physico-mechanical testing chamber in simulated environments of deep earth, deep space, and deep sea provided by the present application comprises a cabin body having a hexahedral structure and 6 butting indenters, wherein the cabin body has an internal space, and an outer wall of the cabin body is provided with an air inlet and an air outlet; the 6 butting indenters are pairwise located in an X-axis direction, a Y-axis direction and a Z-axis direction; the 6 butting indenters are respectively mounted in through holes on six faces of the cabin body, inner ends of the butting indenters extend into the cabin body, outer ends of the butting indenters are exposed out of the cabin body, and the butting indenters can axially move relative to the cabin body.

Particularly, the outer wall of the cabin body is provided with a cold source port.

Optionally, the air inlet is operatively connected to a hot air source, or the cold source port is operatively connected to a liquid nitrogen supply system.

Optionally, the cabin body comprises an outer cubic frame and 6 panels, and the 6 panels are respectively mounted in 6 directions of the outer cubic frame;

an outer side of each panel is provided with an elastic plate, two ends of the elastic plate are movably connected to the outer cubic frame, coaxial through holes are formed in the elastic plate and the panel, the butting indenters are mounted in the through holes and fixedly connected to the elastic plate, and a gap is formed between the elastic plate and an outer surface of the panel.

Optionally, at least two strip-shaped notches are formed at the two ends of the elastic plate, adapted clamping pins are mounted at a position that is of the outer cubic frame and that corresponds to the strip-shaped notches, and the two ends of the elastic plate are respectively clamped on the clamping pins through the strip-shaped notches.

Particularly, a heating plate is mounted at a front end of at least one of the butting indenters, and an electric heating element is mounted in the heating plate.

The rock physico-mechanical testing and three-dimensional multi-field information perception cabin in simulated environments of deep earth, deep space, and deep sea provided by the present application comprises an elastic pressure box and the rock physico-mechanical testing chamber in simulated environments of deep earth, deep space, and deep sea, wherein the elastic pressure box is operatively placed in the cabin body; the elastic pressure box comprises 6 indenters, and rear ends of the 6 indenters are each butted with one of the butting indenters; the indenter is provided with a temperature sensor and/or a heat flow sensor; and a displacement detection mechanism is or is not provided between the two indenters in the same axial direction.

Particularly, the indenter comprises an indenter body and a permeation block, wherein a front end of the indenter body is provided with an annular sealing groove and a rectangular convex block, the annular sealing groove is located at an edge of the front end of the indenter body, the rectangular convex block is located on an inner periphery of the annular sealing groove, and a circumferential sealing strip is embedded in the annular sealing groove;

a percolation medium channel and a sealing medium injection channel are arranged in the indenter body, one end of the sealing medium injection channel is communicated with the annular sealing groove, and the other end of the sealing medium injection channel passes through an outer surface of the indenter body; and a front end face of the rectangular convex block is provided with an integrally-manufactured embedding groove, the permeation block is embedded in the embedding groove, a plurality of permeation holes are uniformly distributed in the permeation block, the permeation holes are communicated with the permeation block from front to back, one end of the percolation medium channel is communicated with the embedding groove, and the other end of the percolation medium channel is communicated with the outer surface of the indenter body.

Particularly, the rock physico-mechanical testing and three-dimensional multi-field information perception cabin in simulated environments of deep earth, deep space, and deep sea further comprises a sample holder, wherein the sample holder comprises a rigid outer cubic frame and a flexible inner cubic frame, the rigid outer cubic frame and the flexible inner cubic frame are both provided with 12 frame edges, 6 faces of the rigid outer cubic frame and 6 faces of the flexible inner cubic frame are both rectangular frames, and 12 outside corner positions of the flexible inner cubic frame are attached to 12 inside corners of the rigid outer cubic frame;

each face of the flexible inner cubic frame is provided with an integrally-manufactured annular flange, wherein the annular flange is adapted to an annular groove of the circumferential sealing strip; and the sample may be loaded in the flexible inner cubic frame, 6 indenters respectively pass through frame openings of the rigid outer cubic frame and the flexible inner cubic frame in 6 directions, and annular flanges on 6 faces of the flexible inner cubic frame are correspondingly loaded in annular grooves of circumferential sealing strips of the 6 indenters.

Optionally, 12 elastic pieces are used to connect 6 indenters together, and a periphery of each indenter is connected to 4 indenters on the periphery through one elastic piece.

Compared with the prior art, the present application has the following beneficial effects:

1. the rock physico-mechanical testing chamber in simulated environments of deep earth, deep space, and deep sea according to the present application can provide a high-temperature environment for a sample by introducing hot air into a cabin body through an air inlet, which is favorable for constructing an even environment temperature, so that the sample is heated uniformly, and the accuracy of a testing result can be improved;
2. according to the present application, an outer wall of the cabin body is provided with a cold source port, so that a cold source can be injected into the cabin body, and a low-temperature environment can be provided for a sample;
3. the rock physico-mechanical testing chamber in simulated environments of deep earth, deep space, and deep sea according to the present application can be butted with a three-axis six-direction stress loading system and can also be butted with an elastic pressure box, the force of the loading system can be transferred to a sample, and the testing chamber is matched with the three-axis six-direction stress loading system for use, so that the reservoir rock mechanical behavior testing under high and low environments can be achieved in real time, which can fill the gap in this field;
4. a sample can be placed in the rock physico-mechanical testing and three-dimensional multi-field information perception cabin in simulated environments of deep earth, deep space, and deep sea according to the present application, the indenters in 6 directions can uniformly transfer pressure to the sample from three axes and six directions, and the temperature of the tested sample can be detected, fed back and adjusted; and
5. the rock physico-mechanical testing and three-dimensional multi-field information perception cabin in simulated environments of deep earth, deep space, and deep sea according to the present application adopts a unique three-way sealing structure, can perform experiments such as stress loading and three-dimensional percolation, and has strong functions.

BRIEF DESCRIPTION OF DRAWINGS

The drawings illustrated herein are used to provide a further understanding of the embodiments of the present application, constitute a part of the present application, and do not constitute a limitation to the embodiments of the present invention.

Figure 1:
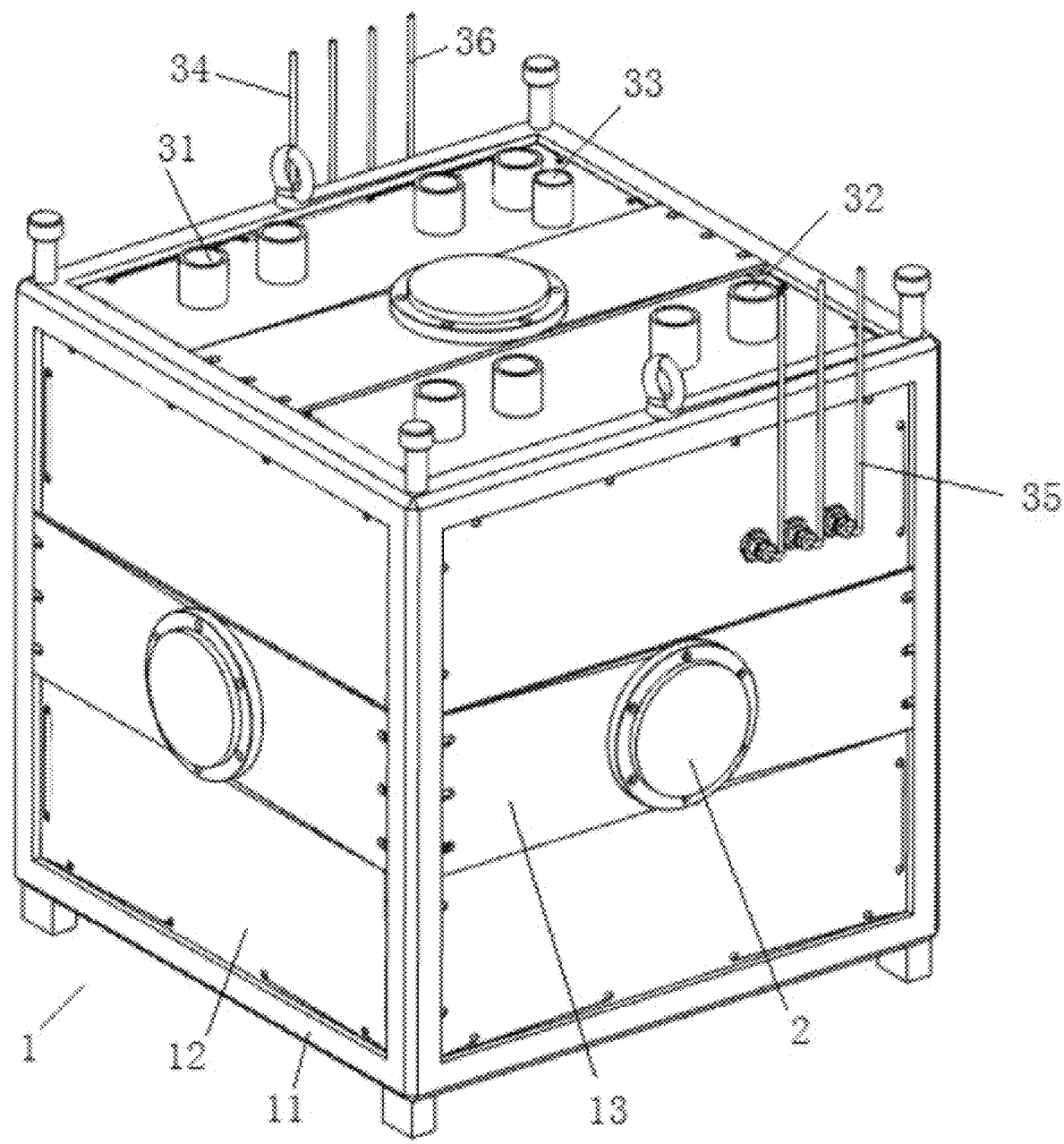
FIG. 1 is a three-dimensional view of a rock physico-mechanical testing chamber in simulated environments of deep earth, deep space, and deep sea according to an embodiment.

in the drawings: 1: cabin body, 11: outer cubic frame, 12: panel, 13: elastic plate, 14: gap, 15: through hole, 111: sinking groove, 112: clamping pin, 121: flange, 122: notch, 131: strip-shaped notch;

2: butting indenter, 21: cylindrical press rod, 22: ball head;

31: air inlet, 32: air outlet, 33: cold source port, 34: percolation inlet pipe, 35: three percolation outlet pipes, 36: sealing main pipe; 4: heating plate, 41: electric heating element;

5: indenter, 51: indenter body, 52: permeation block, 53: circumferential sealing strip, 54: thermal conductive pad, 55: temperature sensor, 56: heat flow sensor, 511: rectangular convex block, 512: percolation medium channel, 513: sealing medium injection channel, 514: annular sealing groove, 515: embedding groove, 521: permeation hole, 531: annular groove;

6: elastic piece;

7: sample holder, 71: rigid outer cubic frame, 72: flexible inner cubic frame, 721: frame edge, 722: annular flange, 723: outside corner position, 724: right-angle edge structure;

8: sample;

9: displacement detection mechanism, 91: displacement sensor, 92: extensometer rod, 93: sensor connecting arm; and

100: hot air source, 200: liquid nitrogen supply system, 300: elastic pressure box.

DETAILED DESCRIPTION OF EMBODIMENTS

To make objectives, technical solutions, and advantages of the present application clearer, the following clearly and completely describes technical solutions in embodiments of the present invention with reference to accompanying drawings in embodiments. It is clear that the described embodiments are merely some but not all of embodiments of the present invention. Generally, components of embodiments of the present invention described and shown in the accompanying drawings herein may be arranged and designed in various configurations.

Therefore, the following detailed descriptions of embodiments of the present invention provided in the accompanying drawings are not intended to limit the scope of the present invention that claims protection, but merely to represent selected embodiments of the present invention. Based on the embodiments of the present invention, all other embodiments obtained by those of ordinary skill in the art without creative effort shall fall within the protection scope of the present invention.

It should be noted that the embodiments and features in the embodiments of the present invention can be combined with each other without conflict. It should be noted that the embodiments in the specification are all described in a progressive manner, and each embodiment focuses on differences from other embodiments, and portions that are the same and similar between the embodiments may be referred to each other.

In the description of the present invention, it should be noted that an orientation or position relationship indicated by terms "upper", "lower", "inner", "outer", or the like is an orientation or position relationship based on the accompanying drawings, or an orientation or position relationship that the product of the present invention is usually placed when in use, or an orientation or positional relationship commonly understood by those skilled in the art. These terms are merely used to facilitate and simplify description of the present invention, instead of indicating or implying that a mentioned apparatus or element must have a specific orientation or be constructed and operated in a specific orientation, and therefore the terms cannot be construed as a limitation on the present invention. In addition, the terms "first", "second" and the like are merely intended for differentiated description, and should not be construed as an indication or an implication of relative importance.

In descriptions of the present invention, it should be further noted that, unless otherwise expressly specified and limited, terms "arranged", "mount", "interconnect" and "connect" should be understood in a broad sense. For example, such terms may indicate a fixed connection, a detachable connection, or an integral connection; may indicate a mechanical connection or an electrical connection; and may indicate direct interconnection, indirect interconnection through an intermediate medium, or internal communication between two elements. For those of ordinary skill in the art, the specific meanings of the aforementioned terms in the present invention can be understood according to specific conditions.

Figure 2:
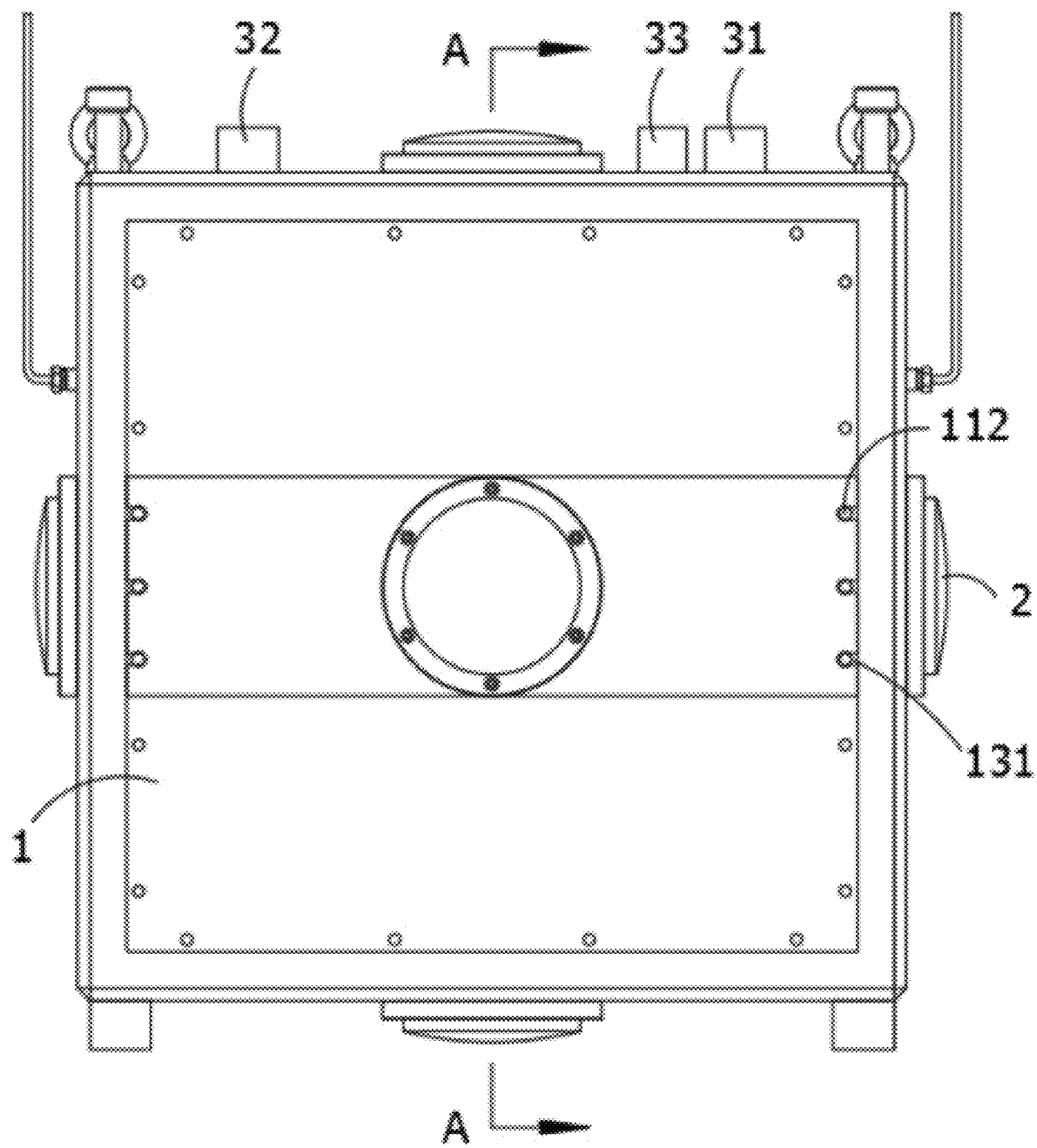
FIG. 2 is a front view of a rock physico-mechanical testing chamber in simulated environments of deep earth, deep space, and deep sea according to an embodiment.
Figure 3:
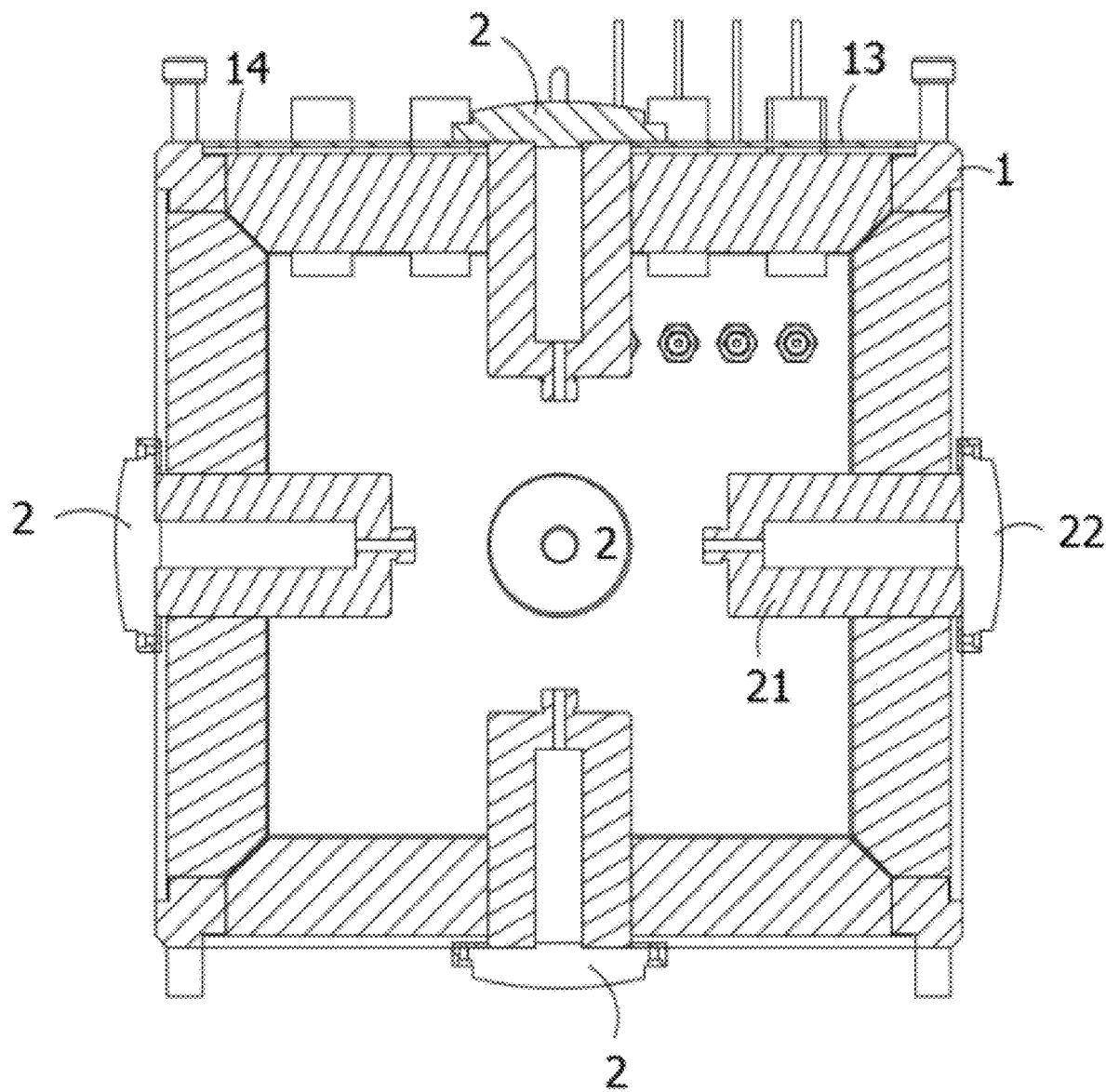
FIG. 3 is a cross-sectional view at A-A in FIG. 2.
Figure 23:
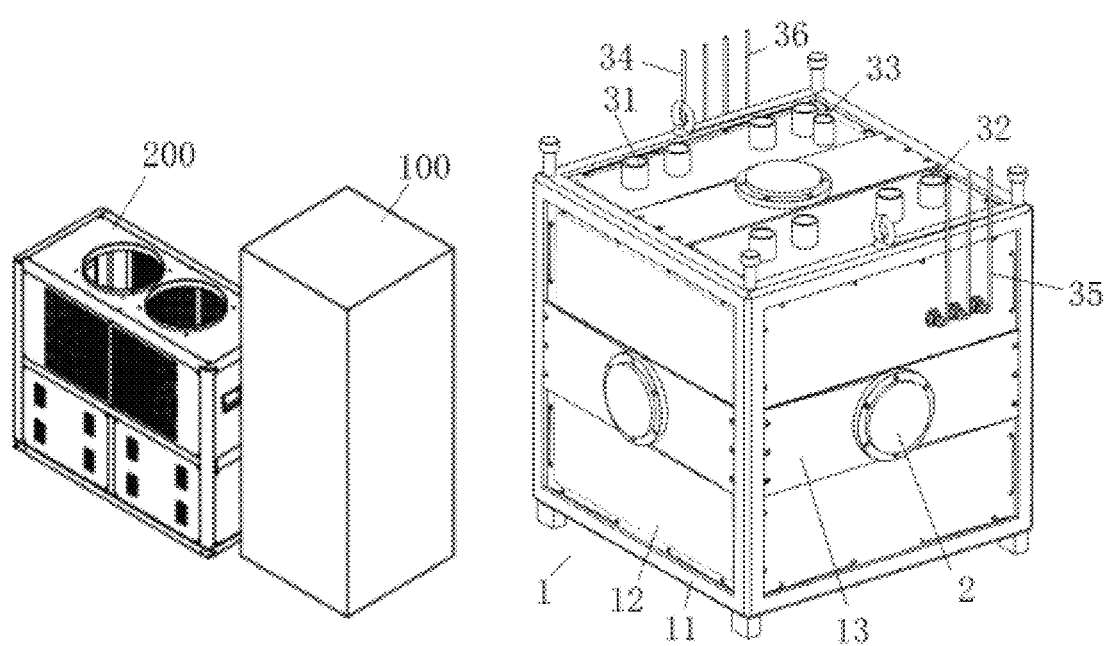
FIG. 23 is a schematic diagram of structures of a cabin body, a hot air source and a liquid nitrogen supply system according to an embodiment.

As shown in FIGS. 1 to 3, the rock physico-mechanical testing chamber in simulated environments of deep earth, deep space, and deep sea disclosed in this embodiment comprises a cabin body 1 having a hexahedral structure, wherein the cabin body 1 has an internal space. An outer wall of the cabin body 1 is provided with an air inlet 31 and an air outlet 32, an air source is connected to the air inlet 31, air with different temperatures can be injected into the cabin body 1 to control the internal temperature, and the injected air is sent out from the air outlet 32. For example, as shown in FIG. 23, the air inlet 31 is connected to a hot air source 100 to inject hot air inside to heat the internal space.

It should be noted that a number of the air inlets 31 and the air outlets 32 is set reasonably based on a requirement. In a possible design, 4 air inlets 31 and 4 air outlets 32 are provided.

In a possible design, the air inlet 31 and the air outlet 32 are arranged on the same face of the cabin body 1. Particularly, a row of air inlets 31 and a row of air outlets 32 are arranged on two sides of a top of the cabin body 1.

To facilitate connection to an air source pipeline, an outer end of the air inlet 31 is connected to an air inlet joint, and an outer end of the air outlet 32 is connected to an air outlet joint.

In a possible design, the outer wall of the cabin body 1 is provided with a cold source port 33, the cold source port 33 is connected to a cold source, and the cold source can be injected into the cabin body 1, so that the internal temperature can be controlled. For example, as shown in FIG. 23, the internal space can be cooled by injecting liquid nitrogen into the cabin body 1 through the cold source port 33 by using a liquid nitrogen supply system 200; and a part of the injected liquid nitrogen becomes gas and may be discharged from the air inlet 31 and the air outlet 32.

In a possible design, the air inlet 31, the air outlet 32 and the cold source port 33 are all arranged at the top of the cabin body 1.

In a possible design, the rock physico-mechanical testing chamber in simulated environments of deep earth, deep space, and deep sea further comprises 6 butting indenters 2, wherein the 6 butting indenters 2 are pairwise located in an X-axis direction, a Y-axis direction and a Z-axis direction and are respectively located on six faces of the cabin body 1. The 6 butting indenters 2 are respectively mounted in through holes on six faces of the cabin body 1, inner ends of the butting indenters 2 extend into the cabin body 1, outer ends of the butting indenters are exposed out of the cabin body 1, and the butting indenters 2 can axially move relative to the cabin body 1.

It should be noted that the three axes herein refer to an X axis, a Y axis and a Z axis in a three-axis coordinate system, respectively. In a possible design, an inner end of the butting indenter 2 is a cylindrical indenter 21, and an outer end is a ball head 22 that is butted with an actuator indenter.

In a possible design, as shown in FIGS. 1 to 4, the cabin body 1 comprises an outer cubic frame 11 and 6 panels 12, the cabin body 1 is integrally mounted by the outer cubic frame 11 with high rigidity, and the outer cubic frame 11 is integrally-manufactured, so that the stability of an entire system can be ensured; and panels 12 are provided in 6 directions of the outer cubic frame 11 and screwed to the outer cubic frame 11, and 6 butting indenters 2 are each mounted in a center of one of the panels 12. The panel 12 is preferably of a thermal insulation material.

In a possible design, an outer side of each panel 12 is provided with an elastic plate 13, two ends of the elastic plate 13 are movably connected to the outer cubic frame 11, coaxial through holes 15 are formed in the elastic plate 13 and the panel 12, the butting indenters 2 are mounted in the through holes 15, the butting indenters 2 are fixedly connected to the elastic plate 13 through screws, and a gap 14 is formed between the elastic plate 13 and an outer surface of the panel 12, so that the elastic plate 13 and the butting indenters 2 can axially move inwards by a distance relative to the panel 12.

Figure 4:
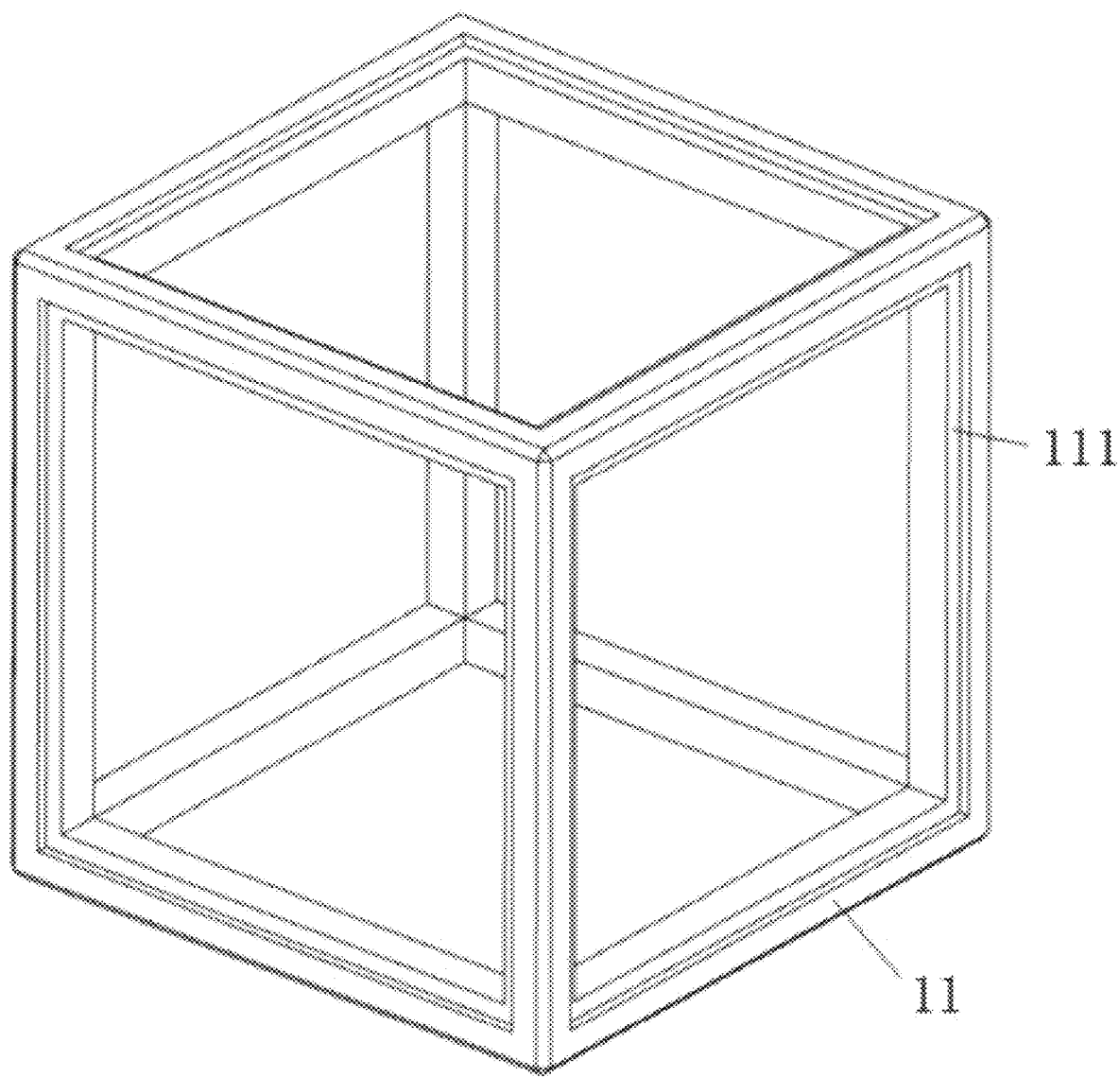
FIG. 4 is a three-dimensional view of an outer cubic frame according to an embodiment.
Figure 5:
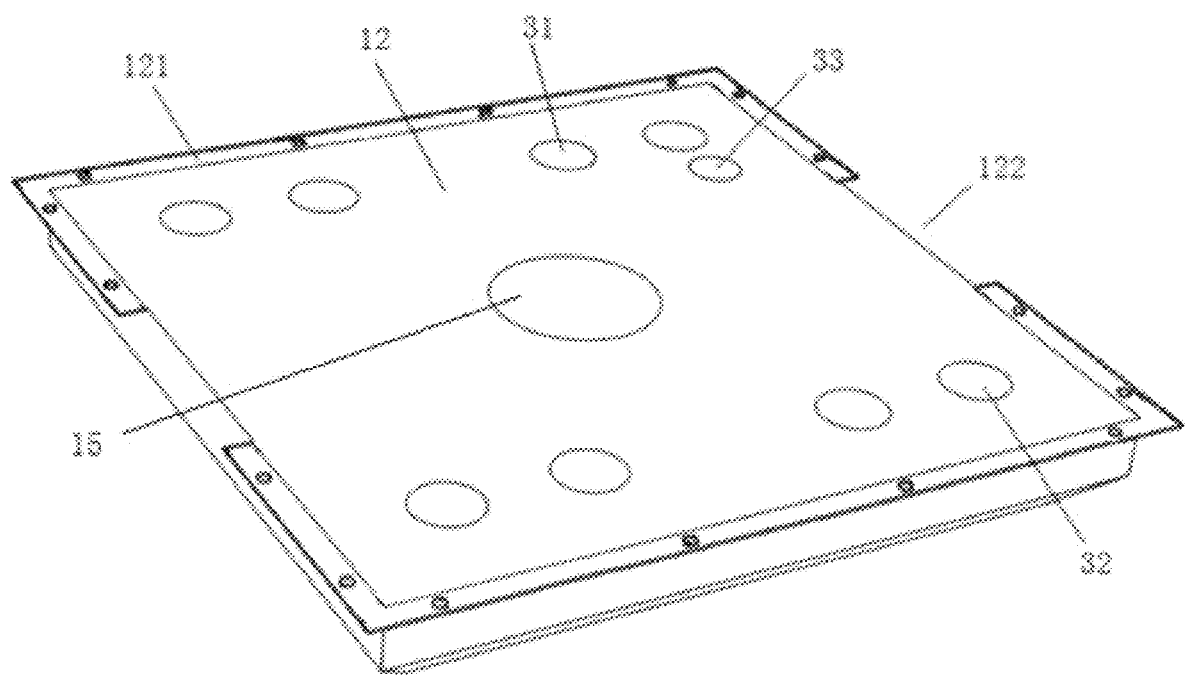
FIG. 5 is a three-dimensional view of a top panel according to an embodiment.

Optionally, as shown in FIGS. 1, 4 and 5, sinking grooves 111 are respectively provided at edges of frame openings of the outer cubic frame 11 in six directions, flanges 121 adapted to the sinking grooves 111 are provided at edges of an outer surface of the panel 2, and the flanges 121 are attached to the sinking grooves 111 and fixedly connected thereto by screws. Particularly, the flange 121 is broken at a position corresponding to the elastic plate 13, thereby forming a notch 122.

Figure 6:
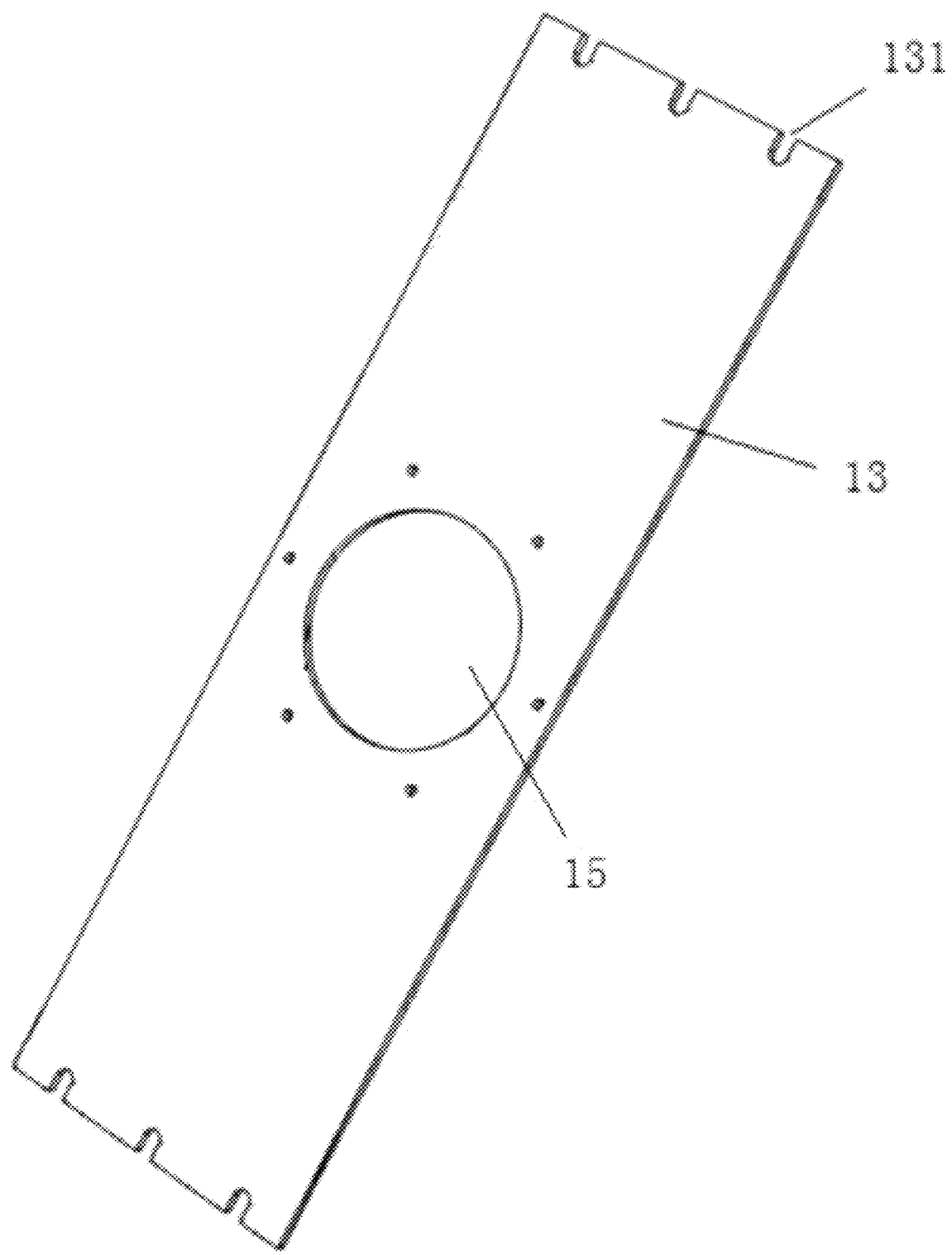
FIG. 6 is a three-dimensional view of an elastic plate according to an embodiment.

Optionally, as shown in FIG. 6, at least two strip-shaped notches 131 are formed at two ends of the elastic plate 13, adapted clamping pins 112 are mounted at a position that is of the outer cubic frame 11 and that corresponds to the strip-shaped notches 131, two ends of the elastic plate 13 are respectively clamped on the clamping pins 112 through the strip-shaped notches 131, so that the elastic plate 13 is movably connected to the outer cubic frame 11, and the clamping pins 112 can slide in the strip-shaped notches 131 under the action of an axial external force. Particularly, the clamping pin 112 is a screw.

Figure 7:
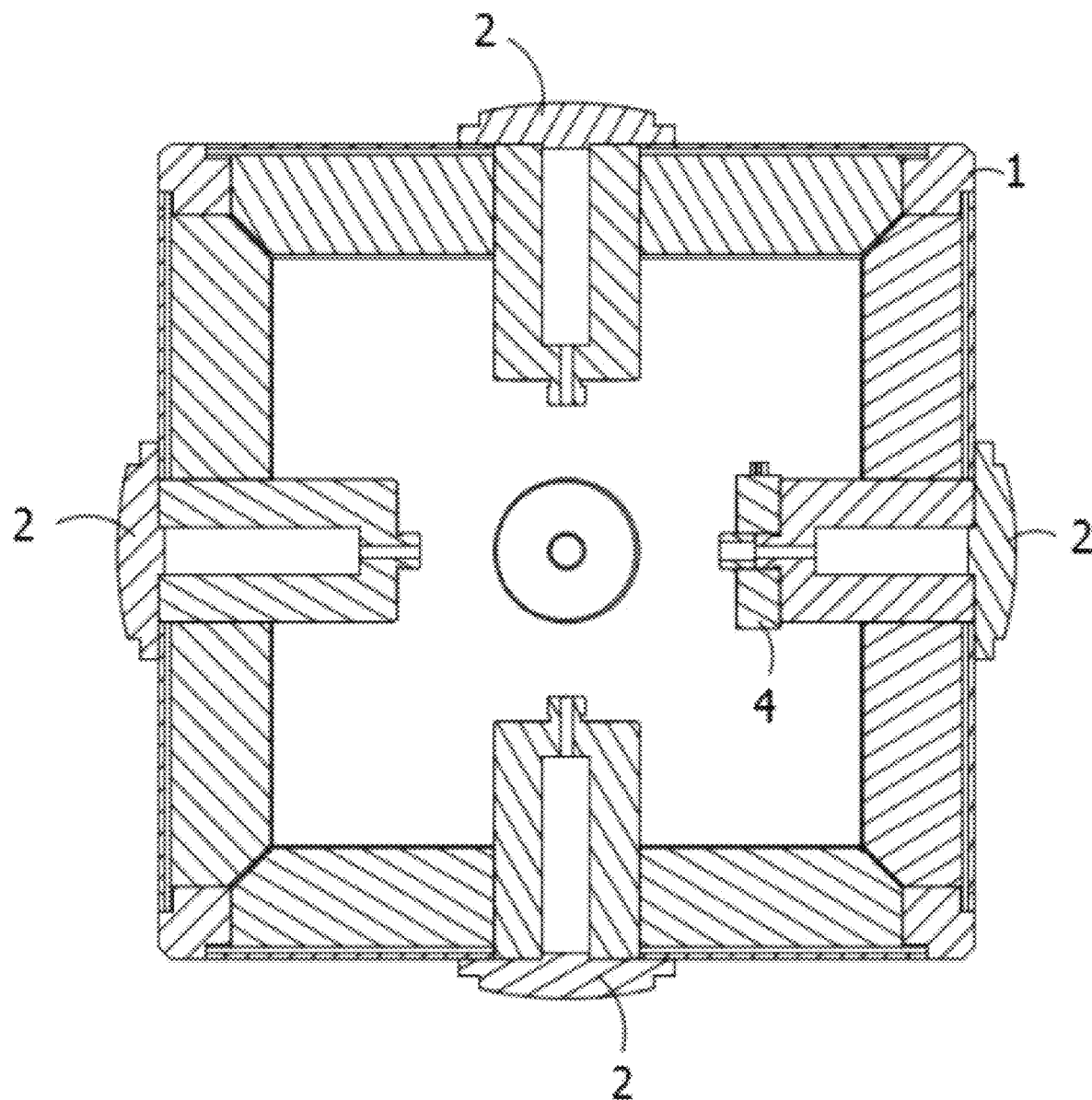
FIG. 7 is a cross-sectional view of a rock physico-mechanical testing chamber in simulated environments of deep earth, deep space, and deep sea according to an embodiment when a heating plate is mounted on one of the butting indenters.
Figure 8:
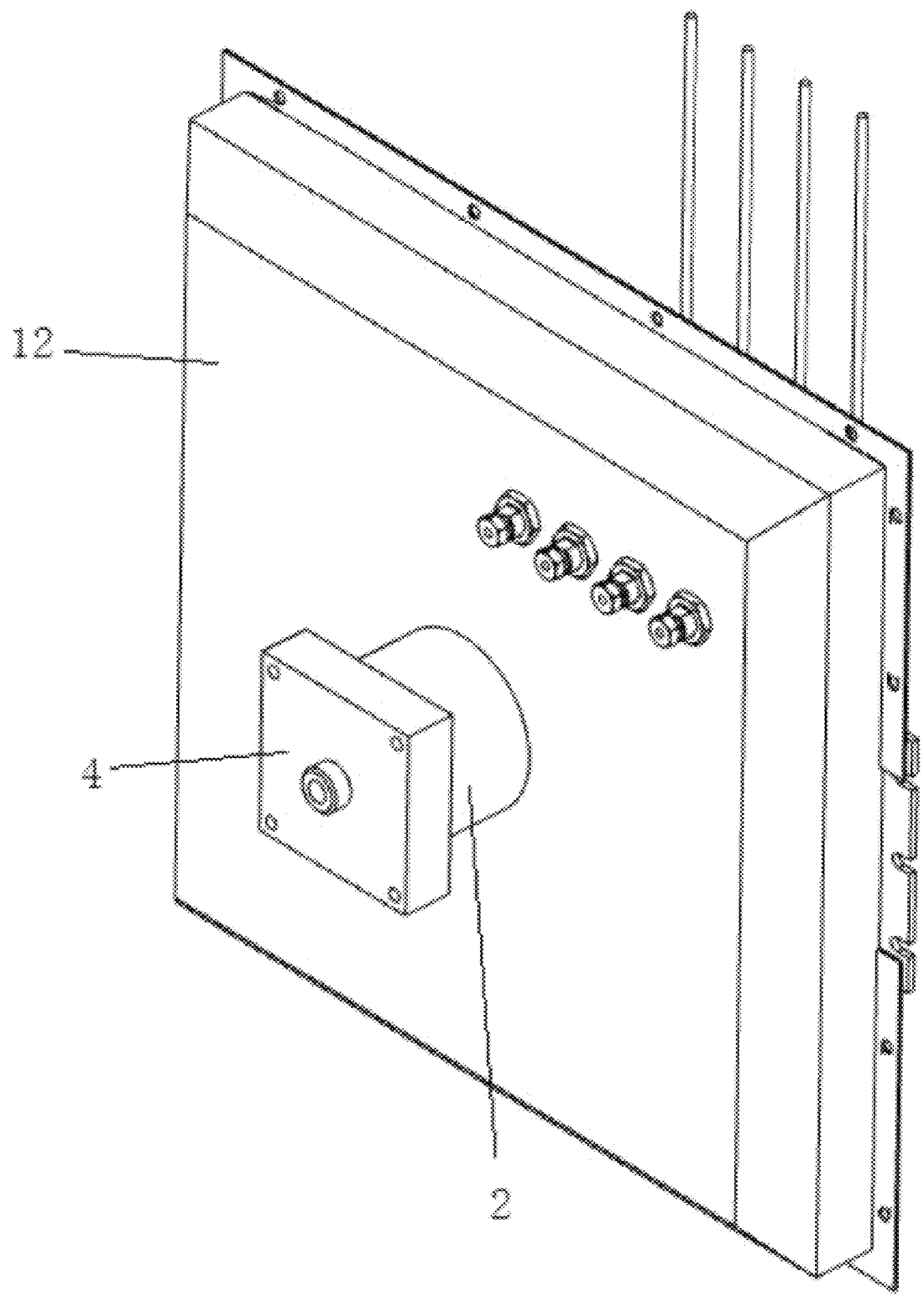
FIG. 8 is a three-dimensional view showing a butting indenter mounted with a heating plate is mounted on a panel according to an embodiment.
Figure 9:
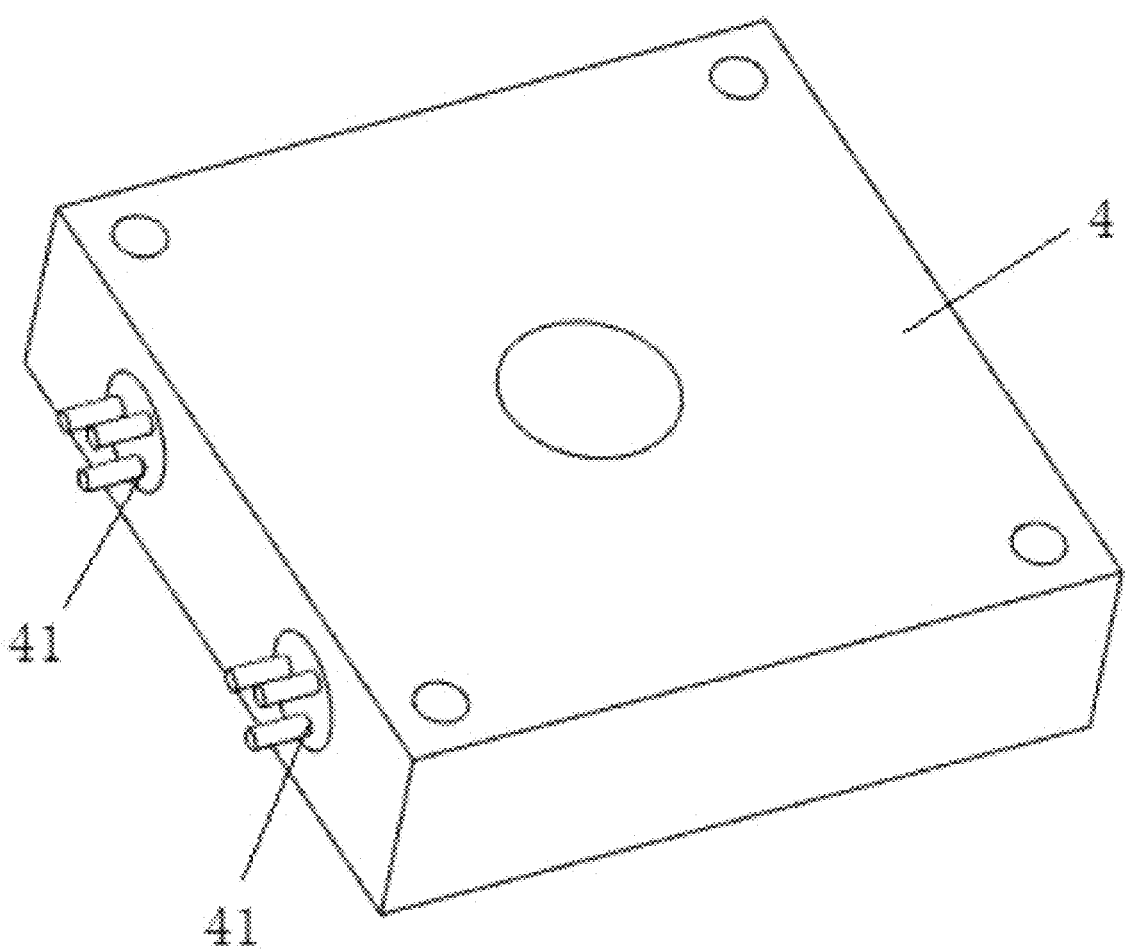
FIG. 9 is a three-dimensional view of a heating plate according to an embodiment.
Figure 10:
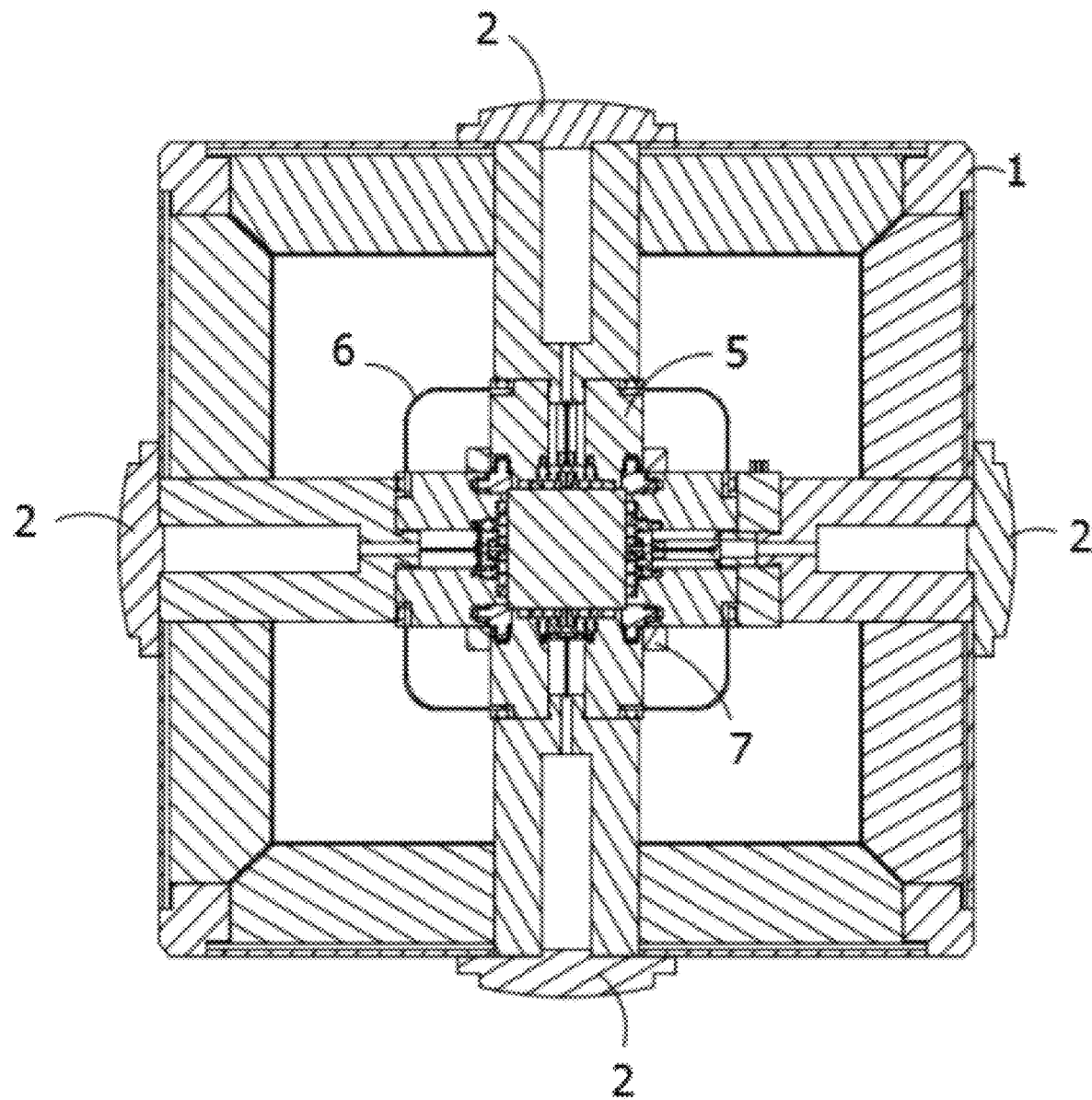
FIG. 10 is a schematic diagram of a structure of a rock physico-mechanical testing and three-dimensional multi-field information perception cabin in simulated environments of deep earth, deep space, and deep sea according to an embodiment.

In a possible design, as shown in FIGS. 7 to 9, a heating plate 4 is mounted at a front end of at least one of the butting indenters 2, and an electric heating element 41 is mounted in the heating plate 4. Optionally, the electrical heating element 41 is an electrical heating rod.

In a possible design, a heating plate 4 is provided at a front end of only one butting indenter 2 for generating opposing temperature differential.

In a possible design, a heating plate 4 is mounted at a front end of each butting indenter 2.

Figure 11:
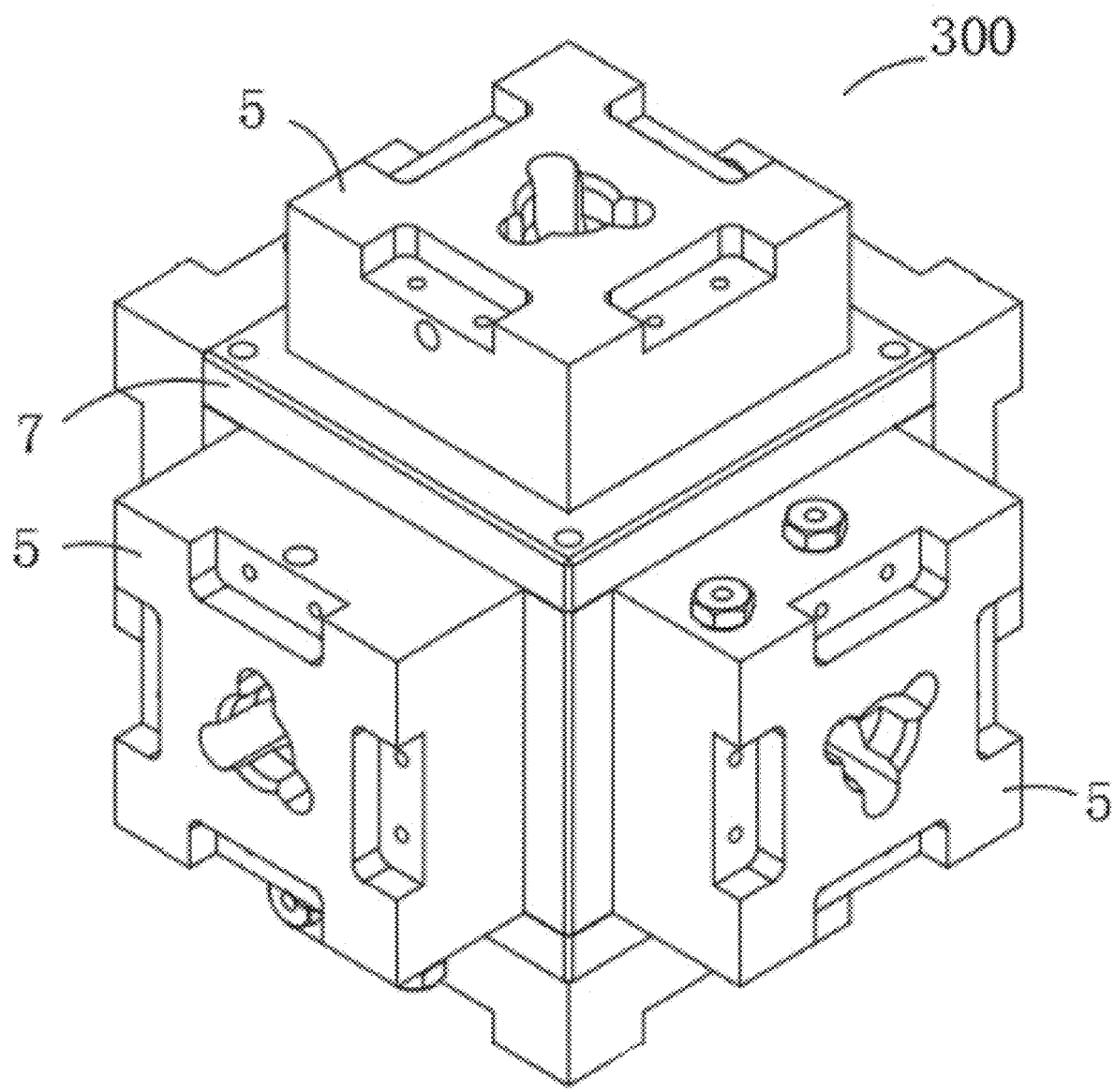
FIG. 11 is a three-dimensional view of an elastic pressure box according to an embodiment.
Figure 12:
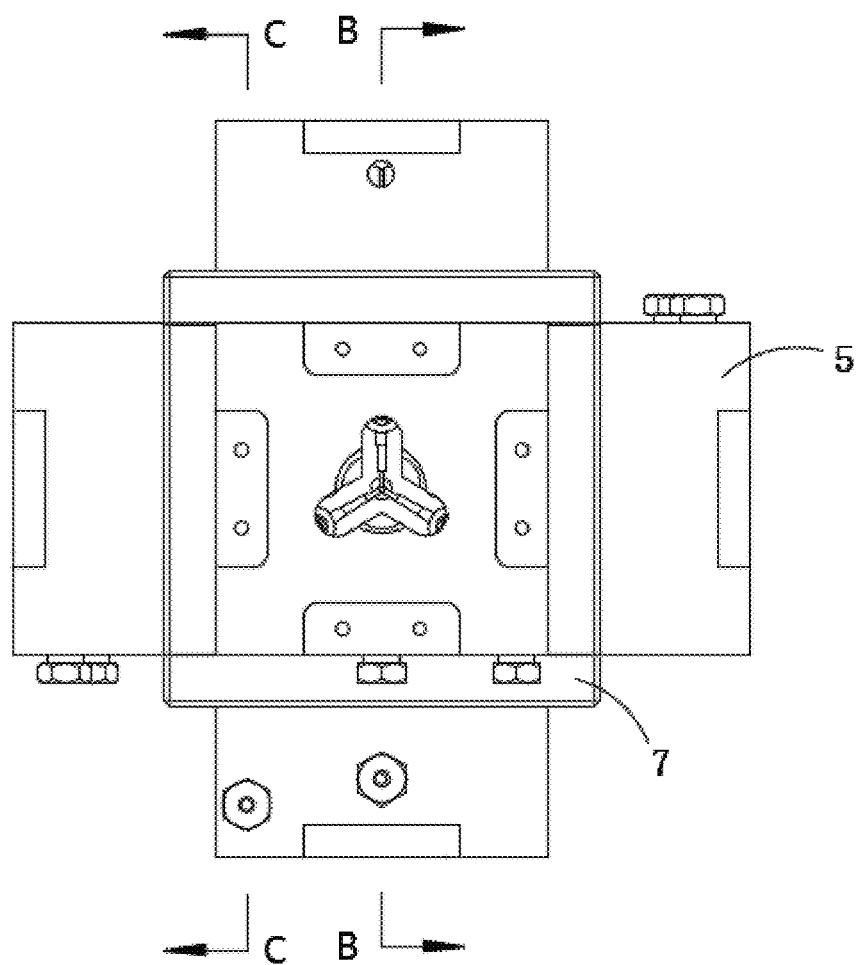
FIG. 12 is a front view of an elastic pressure box according to an embodiment.
Figure 13:
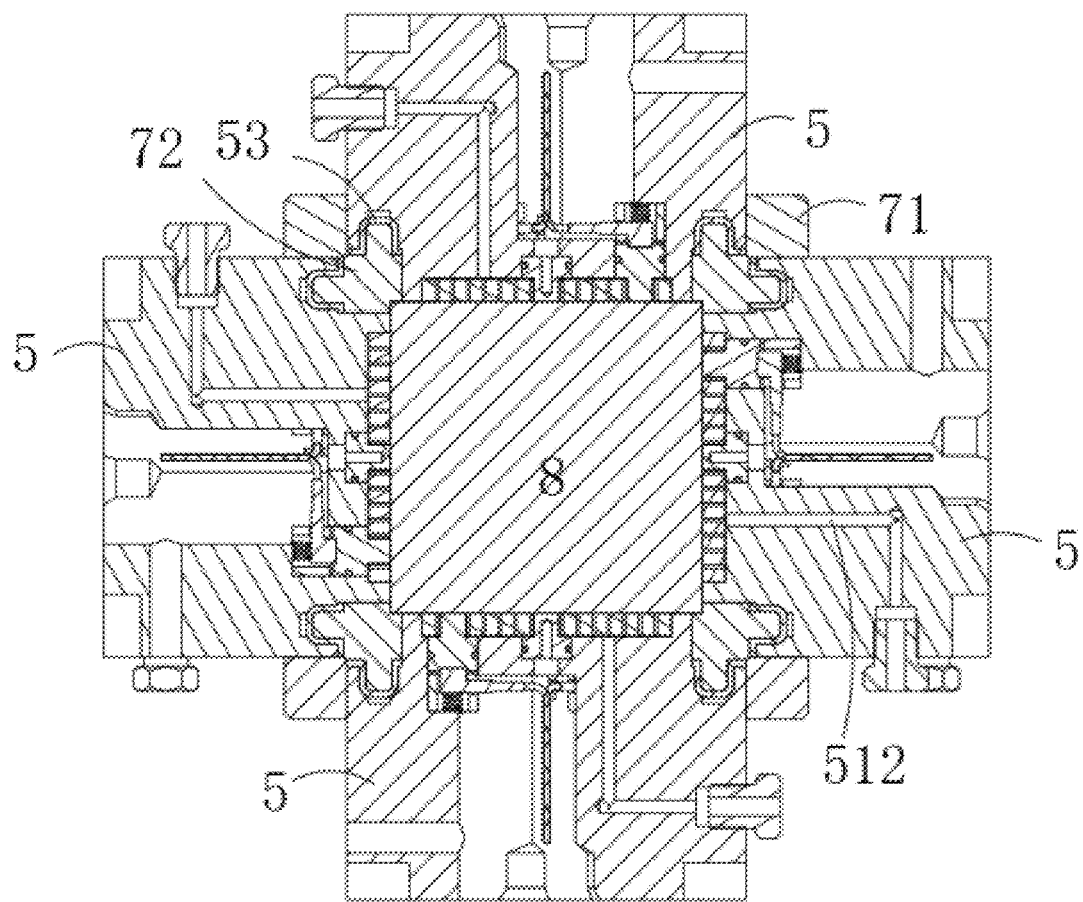
FIG. 13 is a cross-sectional view at B-B in FIG. 12.
Figure 14:
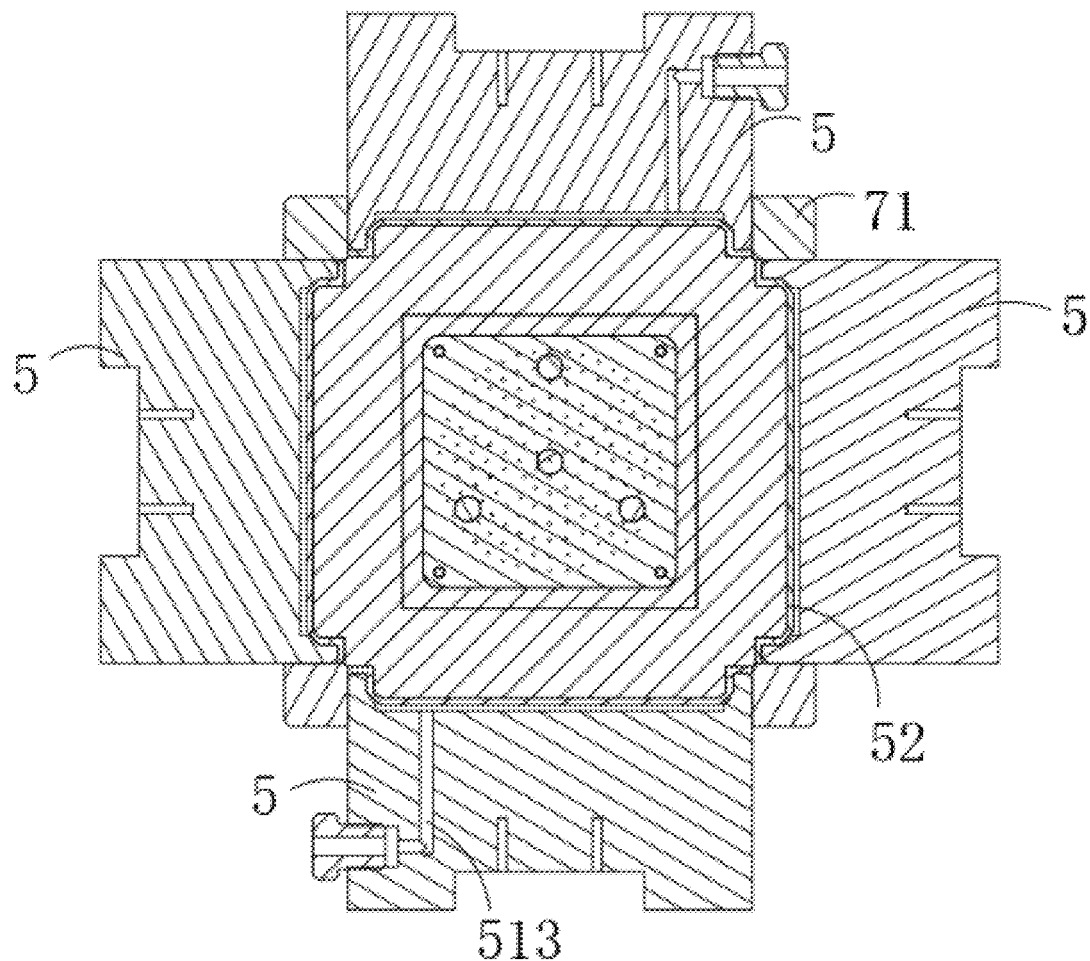
FIG. 14 is a cross-sectional view at C-C in FIG. 13.

As shown in FIG. 11, the rock physico-mechanical testing and three-dimensional multi-field information perception cabin in simulated environments of deep earth, deep space, and deep sea disclosed by this embodiment comprises the rock physico-mechanical testing chamber in simulated environments of deep earth, deep space, and deep sea and an elastic pressure box 300.

As shown in FIGS. 10 to 15, the elastic pressure box 300 comprises 6 indenters 5, and the 6 indenters 5 are pairwise located on three axes, wherein the three axes herein are referred to as an X axis, a Y axis and a Z axis in a three-axis coordinate system. 6 indenters 5 are used to butt with 6 butting indenters 2 of the rock physico-mechanical testing chamber in simulated environments of deep earth, deep space, and deep sea. Of course, a center of a rear end of the 6 indenters 5 is provided with a butting port matched with the butting indenter 2.

In a possible design, the indenter 5 is rectangular. The 6 indenters 5 are respectively adapted to 6 faces of the cubic sample.

In a possible design, a thermal conductive pad 54 is mounted in a hole at a front end of the indenter 5.

In a possible design, a temperature sensor 55 and/or a heat flow sensor 56 resistant to high temperature and high pressure are/is arranged in a middle of the front end of each indenter 5, so that the real-time monitoring of the surface temperature of the sample in the experimental process and the measurement of the heat flow can be achieved.

Particularly, the temperature sensor 55 and the heat flow sensor 56 are integrated on the same probe, and the integrated temperature and heat flow probe is embedded in a center hole of each indenter 5. The thermal conductive pad 54 is mounted at a front end of the center hole of the indenter 5, and the temperature of the sample is transmitted to the integrated temperature and heat flow probe in the center hole through the thermal conductive pad 54.

Figure 15:
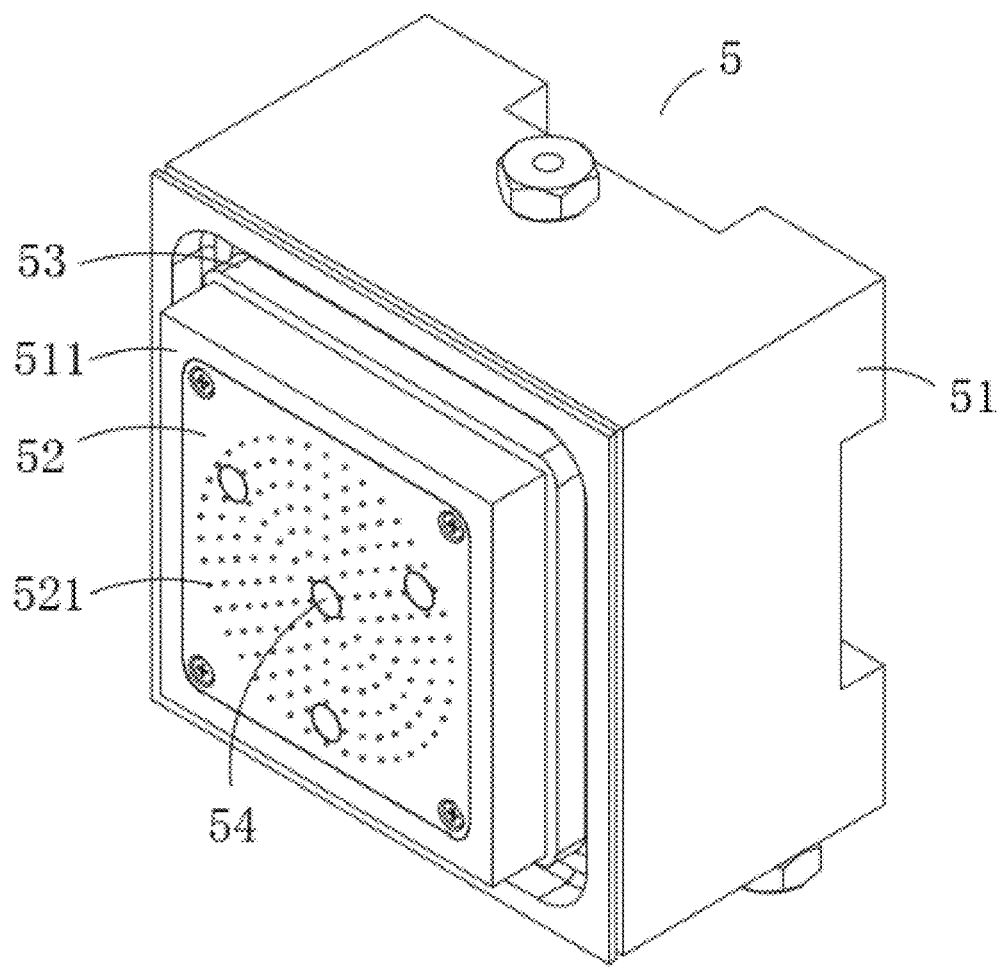
FIG. 15 is a three-dimensional view of an indenter according to an embodiment.
Figure 16:
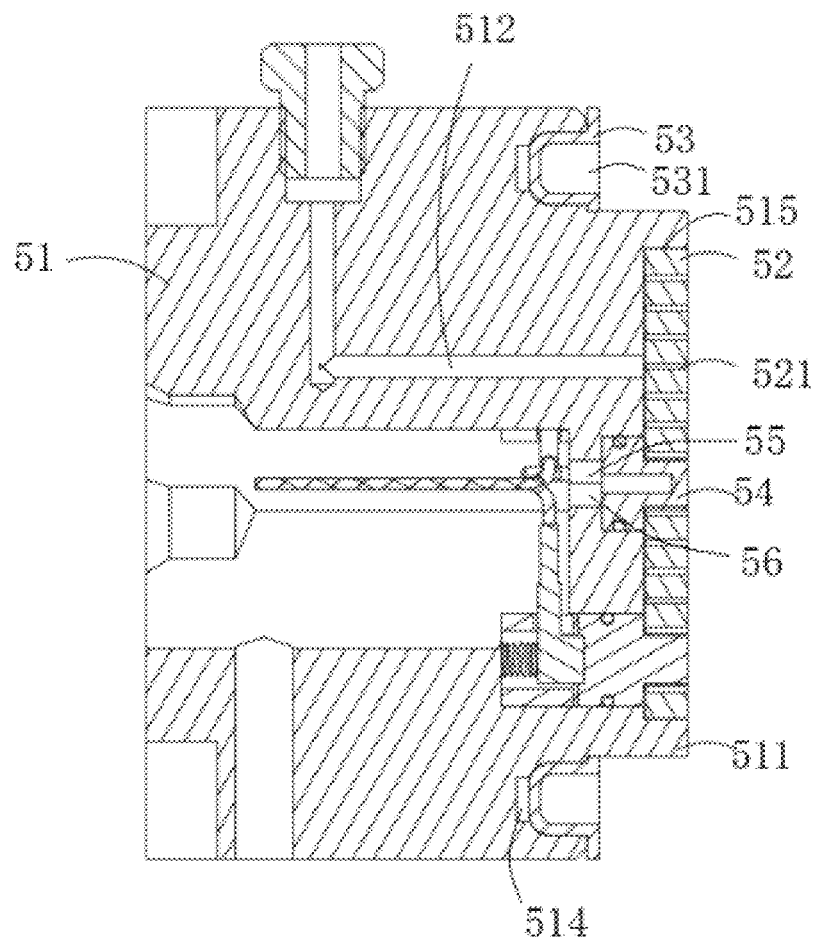
FIG. 16 is a cross-sectional view of an indenter according to an embodiment.

In a possible design, as shown in FIGS. 15 and 16, the indenter 5 comprises an indenter body 51 and a permeation block 52. A front end of the indenter body 51 is provided with an annular sealing groove 514 and a rectangular convex block 511, the annular sealing groove 514 is located at an edge of the front end of the indenter body 51, the rectangular convex block 511 is located on an inner periphery of the annular sealing groove 514, and a circumferential sealing strip 53 is embedded in the annular sealing groove 514. The annular sealing groove 514 and the rectangular convex block 511 are manufactured integrally with the indenter body 51.

A percolation medium channel 512 and a sealing medium injection channel 513 are arranged in the indenter body 51, one end of the sealing medium injection channel 513 is communicated with the annular sealing groove 514, and the other end of the sealing medium injection channel passes through an outer surface of the indenter body 51.

A front end face of the rectangular convex block 511 is provided with an integrally-manufactured embedding groove 515, the permeation block 52 is embedded in the embedding groove 515 through screws, a plurality of permeation holes 521 are uniformly distributed in the permeation block 52, and the permeation holes 521 are communicated with the permeation block 52 from front to back.

One end of the percolation medium channel 512 is communicated with the embedding groove 515, and the other end of the percolation medium channel is communicated with the outer surface of the indenter body 51. Percolation media with different temperatures and pressures can be injected through the percolation medium channel 512 according to experimental requirements, and the percolation media flow into the embedding groove 515 and then uniformly flow to the sample through a plurality of permeation holes 521. A high-pressure sealing medium can be injected into the annular sealing groove 514 through the sealing medium injection channel 513, so that percolation medium can be prevented from flowing out from an edge of the sample, which can be used for rock mass percolation testing.

In a possible design, the permeation block 52 is provided with a plurality of circles of permeation holes 521 that are equally spaced and concentric from inside to outside, and each circle is provided with a plurality of permeation holes 521 that are equally spaced along a circumferential direction.

In a possible design, the sealing medium injection channel 513 and the percolation medium channel 512 are L-shaped, and the other ends thereof vertically pass through a sidewall of the indenter body 51. Optionally, the entire indenter body 51 is made of a high-rigidity alloy material. The permeation block 52 also has high rigidity.

Figure 17:
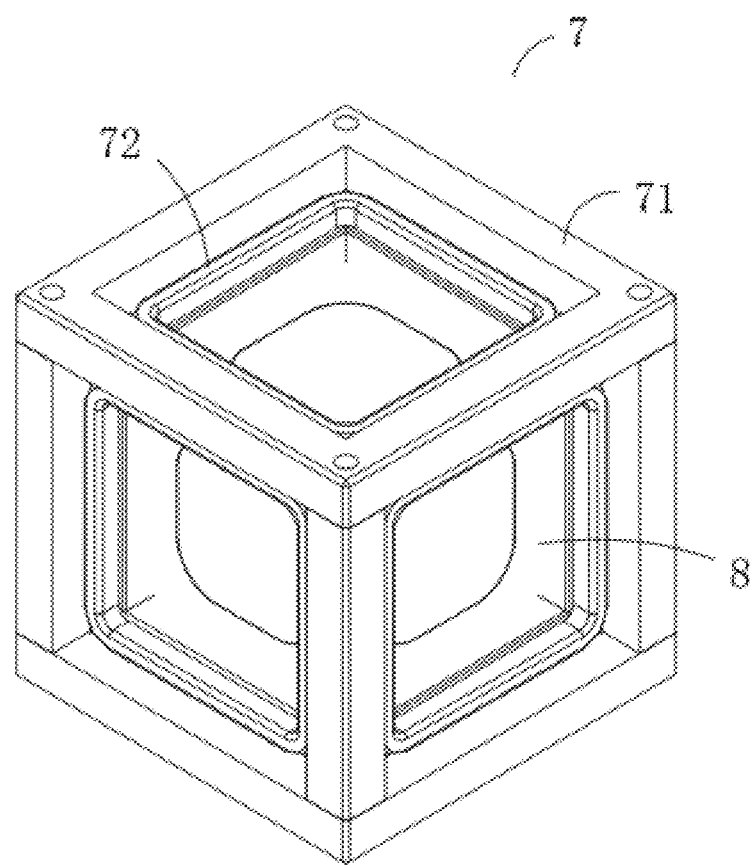
FIG. 17 is a three-dimensional view of a sample holder according to an embodiment.
Figure 18:
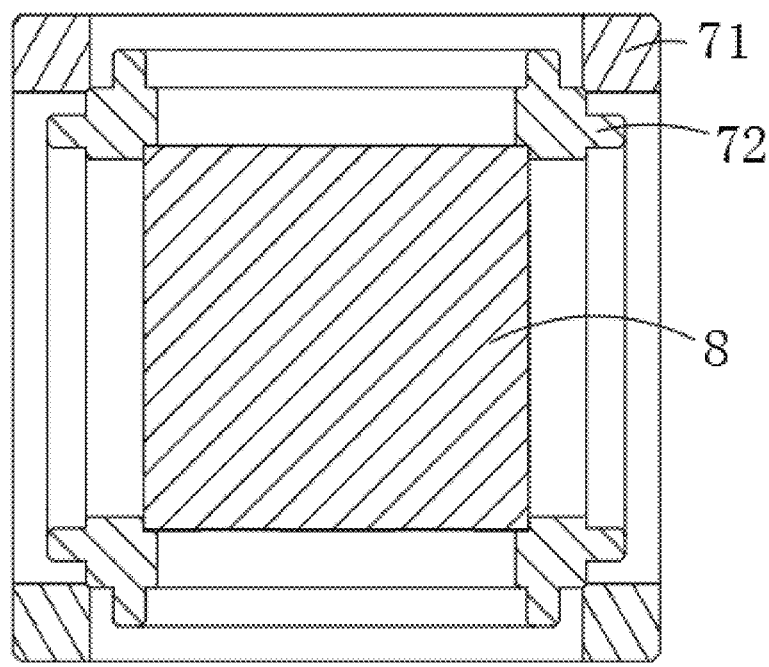
FIG. 18 is a cross-sectional view of a sample holder according to an embodiment.

In a possible design, the elastic pressure box further comprises a sample holder 7. As shown in FIGS. 17 and 18, the sample holder 7 is used to fix a cubic sample 8; meanwhile, openings adapted to 6 indenters 5 need to be reserved in 6 directions.

In a possible design, the sample holder 7 comprises a rigid outer cubic frame 71 and a flexible inner cubic frame 72, the rigid outer cubic frame 71 and the flexible inner cubic frame 72 are both provided with 12 frame edges 721, and 6 faces of the rigid outer cubic frame 71 and 6 faces of the flexible inner cubic frame 72 are both rectangular frames.

The sample 8 may be loaded in the flexible inner cubic frame 72. The 12 outside corner positions 723 of the flexible inner cubic frame 72 are attached to 12 inside corners of the rigid outer cubic frame 71.

In a possible design, the 12 inside corner positions of the flexible inner cubic frame 72 have right-angled edge structures 724 that are adapted to corners of the sample 8.

In a possible design, the flexible inner cubic frame 72 is made of a wear-resistant, pressure-resistant and high-strength rubber frame, and the rigid outer cubic frame 71 is a metal frame.

Figure 19:
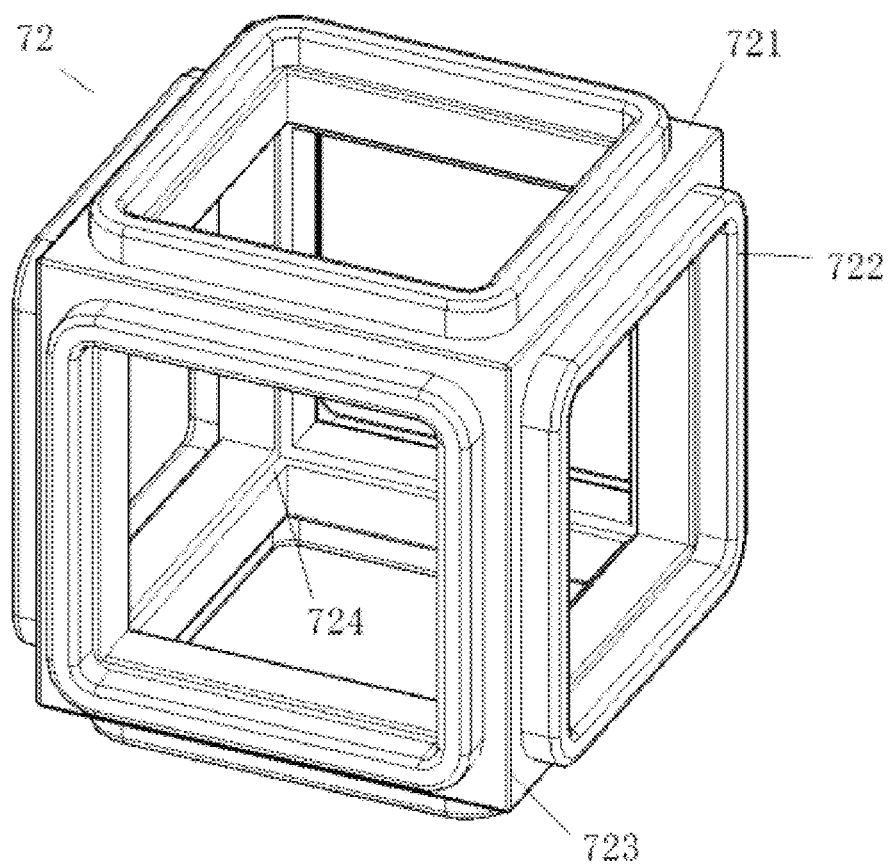
FIG. 19 is a three-dimensional view of a flexible inner cubic frame according to an embodiment.
Figure 20:
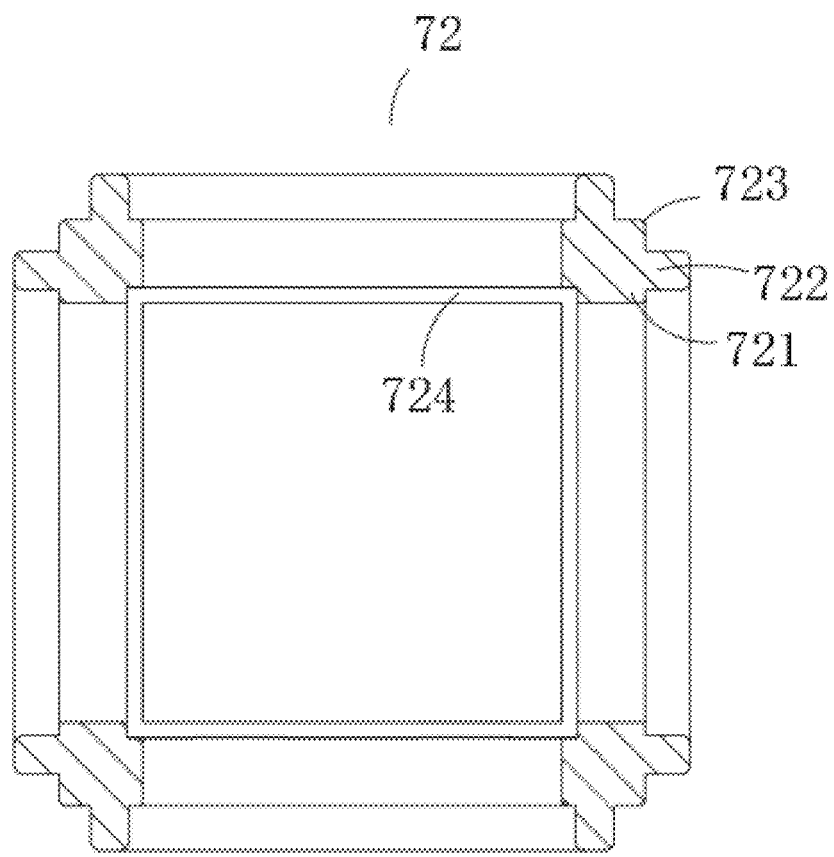
FIG. 20 is a cross-sectional view of a flexible inner cubic frame according to an embodiment.

In a possible design, as shown in FIGS. 18 and 19, each face of the flexible inner cubic frame 72 is provided with an integrally-manufactured annular flange 722, and the annular flange 722 is adapted to the annular sealing groove of the indenter body 51.

As shown in FIG. 16, the circumferential sealing strip 53 is provided with an annular groove 531 that is adapted to the annular flange 722, and the annular flange 722 can be fitted in the annular groove 531 of the circumferential sealing strip 53. Optionally, a cross section of the circumferential sealing strip 53 is a U-shaped structure with an opening facing outward. Particularly, the circumferential sealing strip 53 is made of high-strength rubber.

In the indenter 5 is adapted to a rectangular frame opening of the rigid outer cubic frame 71, and the two may be kept relatively fixed by friction. A rectangular convex block 511 is adapted to a rectangular frame opening of the flexible inner cubic frame 72.

Figure 21:
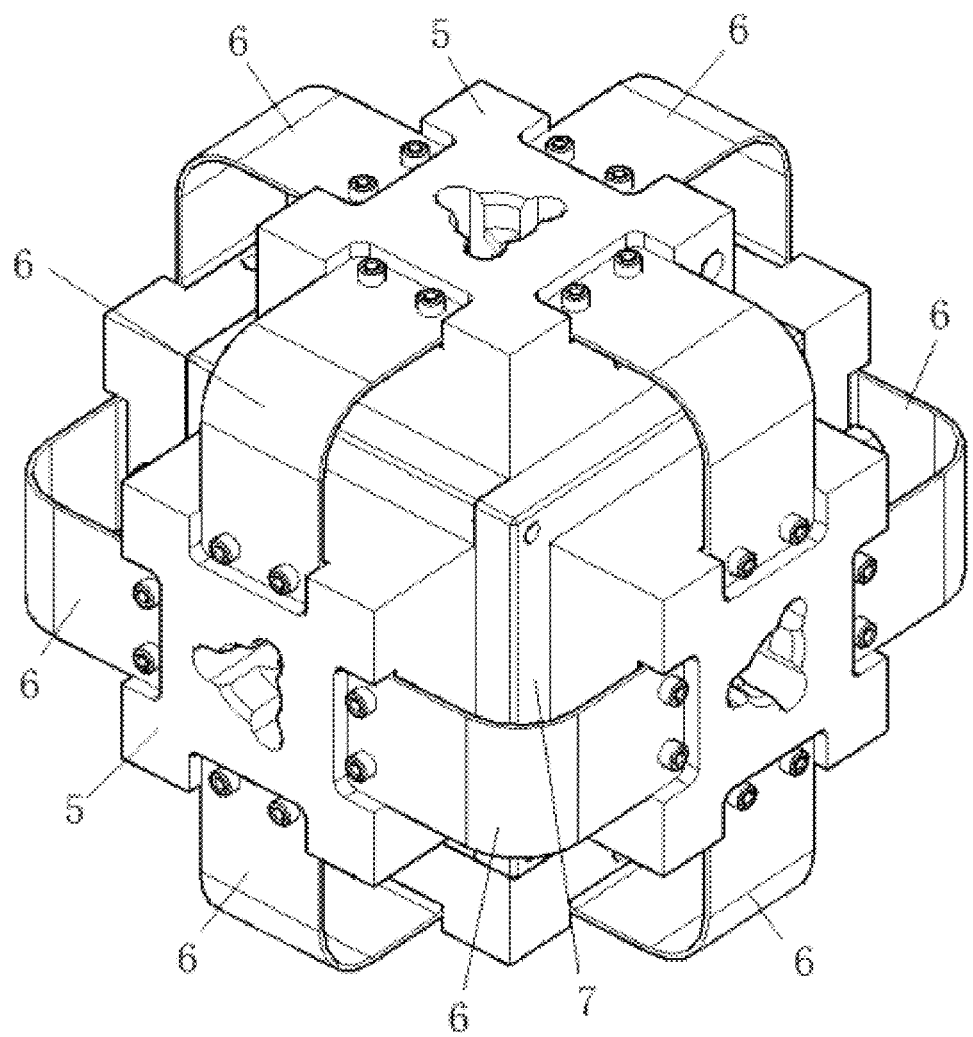
FIG. 21 is a three-dimensional view of elastic pieces connecting indenters together according to an embodiment.

In a possible design, as shown in FIG. 21, at least 8 elastic pieces 6 are used to connect the 6 indenter 5 together such that the inside of the indenters forms a sample space for placing the sample 8.

It should be noted that a number of the elastic pieces 6 is set reasonably based on a requirement. Optionally, 12 elastic pieces 6 are used to connect 6 indenters 5 together, and a periphery of each indenter 5 is connected to 4 indenters 5 on the periphery through one elastic piece 6. Of course, in another possible design, more elastic pieces 6 may be used to connect 6 indenters 5 together.

Optionally, an outer end of the indenter 5 is provided with an elastic piece groove adapted to the elastic plate 6, a screw hole is arranged in the elastic piece groove, and one end of the elastic plate 6 is placed in the elastic piece groove and connected to the indenter 5 through a screw.

In a possible design, the cabin body 1 is provided with three percolation inlet pipes 34, three percolation outlet pipes 35 and a sealing main pipe 36, wherein the three percolation inlet pipes 34 are respectively connected to the percolation medium channels 512 of one of the indenters 5 in the X-axis direction, one of the indenters 5 in the Y-axis direction and one of the indenters 5 in the Z-axis direction, and the three percolation outlet pipes 35 are respectively connected to the percolation medium channels 512 of the other indenter 5 in the X-axis direction, the other indenter 5 in the Y-axis direction and the other indenter 5 in the Z-axis direction. Fluid with different temperatures and pressures can be injected through the percolation medium channel 512 according to experiment requirements, and the fluid can uniformly flow to the sample 8 through the permeation holes 521.

The sealing main pipe 36 is connected to the sealing medium injection channels 513 of the 6 indenters 5 through 6 sealing branch pipes (not shown in the figure). The sealing medium can be injected into the annular sealing groove of the indenter 5 through the sealing medium injection channel 513, and the percolation medium can be prevented from flowing out from the edge of the sample 8.

Figure 22:
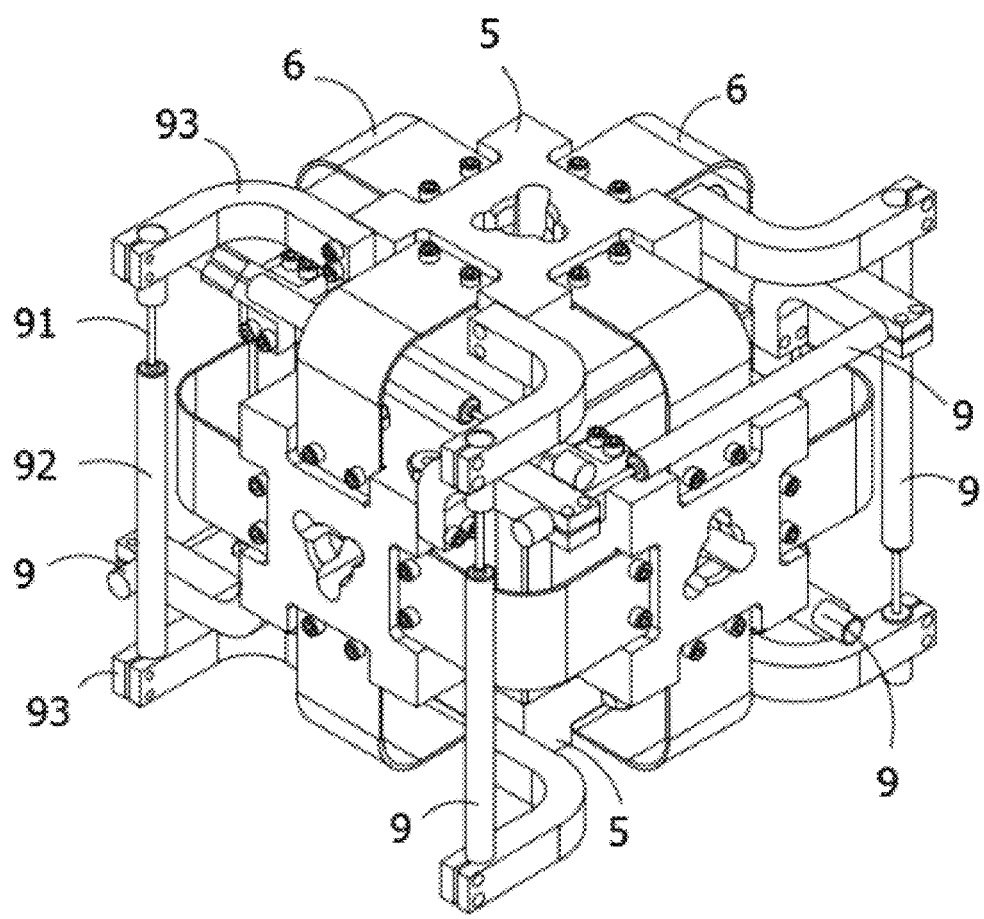
FIG. 22 is a three-dimensional view of an elastic pressure box according to an embodiment when a displacement detection mechanism is provided between each pair of indenters.

In a possible design, as shown in FIG. 22, at least one displacement detection mechanism 9 is provided between two indenters 5 in the X-axis direction, between two indenters 5 in the Y-axis direction and between two indenters 5 in the Z-axis direction, the displacement detection mechanism 9 may monitor the deformation of the sample in real time, and the three-dimensional deformation test of the sample may be achieved through the displacement detection mechanisms 9 in the X, Y and Z directions.

Optionally, two displacement detection mechanisms 9 are each provided between the two indenters 5 in the X-axis direction and between the two indenters in the Y-axis direction, and the two displacement detection mechanisms 9 are respectively mounted at diagonal positions of the two indenters 5; 3 displacement detection mechanisms 9 are provided between the two indenters 5 in the Z-axis direction and are located at three angular positions of the two indenters 5, so that the precise measurement of the deformation of the sample in the Z-axis direction can be achieved.

In a possible design, the displacement detection mechanism 9 comprises a displacement sensor 91, an extensometer rod 92 and two sensor connecting arms 93, wherein the sensor connecting arms 93 are respectively fixed on side portions of two indenters 5 in the same axial direction, one end of the displacement sensor 91 is connected to one of the sensor connecting arms 93, one end of the extensometer rod 92 is connected to the other sensor connecting arm 93, and the other end of the displacement sensor 91 is connected to or contacts the other end of the extensometer rod 92.

In a possible design, the displacement sensor 91 is an LVDT sensor. When the sample 8 is deformed, the two indenters 5 move toward each other, and the extensometer rod 92 pushes the displacement sensor 91 to contract, so that the deformation amount of the sample 8 is detected by the displacement sensor 91.

The rock physico-mechanical testing and three-dimensional multi-field information perception cabin in simulated environments of deep earth, deep space, and deep sea in this embodiment has the following working principle.

In use, a 100×100×100 mm sample 8 is placed within the flexible inner cubic frame 72, wherein 12 outside corner positions 723 of the flexible inner cubic frame 72 are attached to 12 inside corners of the rigid outer cubic frame 71;

6 indenters 5 respectively pass through frame openings of the rigid outer cubic frame 71 and the flexible inner cubic frame 72 in 6 directions, and annular flanges 722 on 6 faces of the flexible inner cubic frame 72 are correspondingly loaded in annular grooves of circumferential sealing strips 53 of the 6 indenters 5;
  an elastic pressure box loaded with the sample is operatively placed in an internal cavity of the cabin body 1, 6 butting indenters 2 are mounted on the cabin body 1, and inner ends of the butting indenters 2 on the cabin body 1 in 6 directions are respectively butted with outer ends of the 6 indenters 5;
  the rock physico-mechanical testing and three-dimensional multi-field information perception cabin in simulated environments of deep earth, deep space, and deep sea is placed in a loading frame of a three-axis six-direction stress loading system, a hydraulic actuator is arranged in each of six directions of the loading frame, and output ends of 6 hydraulic actuators are respectively butted with the outer ends of 6 butting indenters 2;
  the 6 hydraulic actuators operate, and the axial force is uniformly transmitted to the sample 8 through the butting indenters 2 and the indenters 5, so that true triaxial stress preloading is achieved;
  the sealing main pipe 36 is connected to a high-pressure plunger pump, and a sealing medium is injected into the sealing medium injection channels 513 of the 6 indenters 5 through the high-pressure plunger pump, so that 12 edges of the sample 8 are tightly attached to the flexible inner cubic frame 72, and a three-way sealing effect is achieved;
  according to an experiment requirement, if a high-temperature environment is required, hot air is sent into the cabin body 1 to heat the sample 8 inside; if a low-temperature environment is required, liquid nitrogen is injected into the cabin body 1 through the cold source port 33 to cool the sample 8 inside; and
  the percolation medium is injected through the three percolation inlet pipes 34, and the percolation medium flowing through the sample 8 finally flows out through the three percolation outlet pipes 35.

The present application can provide high and low temperature environments for the sample, can detect, feed back and adjust the temperature of the tested sample in real time, and can achieve the reservoir rock mechanical behavior test under high and low temperatures. Therefore, the present application has a wide range of applications and is conducive to popularization.

The objectives, technical solutions and beneficial effects of the present application are further explained in detail with reference to the specific implementations described above, and it should be understood that the above-mentioned contents are merely specific implementations of the present invention, and are not intended to limit the protection scope of the present invention. Any modification, equivalent substitution, improvement and the like made within the spirit and principle of the present invention shall all fall within the protection scope of the present invention.

What is claimed is:

1. A rock physico-mechanical testing chamber in simulated environments of deep earth, deep space, and deep sea, comprising:
  a cabin body having a hexahedral structure, wherein the cabin body has an internal space, and an outer wall of the cabin body is provided with an air inlet and an air outlet; and
  6 butting indenters pairwise located in an X-axis direction, a Y-axis direction and a Z-axis direction in a three-axis coordinate system, wherein the 6 butting indenters are respectively mounted in through holes on six faces of the cabin body, inner ends of the butting indenters extend into the cabin body, outer ends of the butting indenters are exposed out of the cabin body;
  wherein the cabin body comprises an outer cubic frame and 6 panels, and the 6 panels are respectively mounted in 6 directions of the outer cubic frame;
  an outer side of each panel is provided with an elastic plate, two ends of the elastic plate are movably connected to the outer cubic frame, coaxial through holes are formed in the elastic plate and the panel, the butting indenters are mounted in the through holes of the elastic plate and the panel and fixedly connected to the elastic plate, and a gap is formed between the elastic plate and an outer surface of the panel, and the butting indenters can axially move relative to the cabin body;
  wherein the outer wall of the cabin body is provided with a cold source port, the air inlet is operatively connected to a hot air source, or the cold source port is operatively connected to a liquid nitrogen supply system.

2. The rock physico-mechanical testing chamber in simulated environments of deep earth, deep space, and deep sea according to claim 1, wherein at least two strip-shaped notches are formed at the two ends of the elastic plate, adapted clamping pins are mounted at a position that is of the outer cubic frame and that corresponds to the strip-shaped notches, and the two ends of the elastic plate are respectively clamped on the clamping pins through the strip-shaped notches.

3. The rock physico-mechanical testing chamber in simulated environments of deep earth, deep space, and deep sea according to claim 1, wherein a heating plate is mounted at a front end of at least one of the butting indenters, and an electric heating element is mounted in the heating plate.

4. A rock physico-mechanical testing and three-dimensional multi-field information perception cabin in simulated environments of deep earth, deep space, and deep sea, comprising: an elastic pressure box and the rock physico-mechanical testing chamber in simulated environments of deep earth, deep space, and deep sea according to claim 1, wherein the elastic pressure box is operatively placed in the cabin body;
  the elastic pressure box comprises 6 indenters, and rear ends of the 6 indenters are respectively butted with one of the butting indenters; the indenter is provided with a temperature sensor and/or a heat flow sensor; and a displacement detection mechanism is or is not provided between the two indenters in the same axial direction.

5. The rock physico-mechanical testing and three-dimensional multi-field information perception cabin in simulated environments of deep earth, deep space, and deep sea according to claim 4, wherein the indenter comprises an indenter body and a permeation block, a front end of the indenter body is provided with an annular sealing groove and a rectangular convex block, the annular sealing groove is located at an edge of the front end of the indenter body, the rectangular convex block is located on an inner periphery of the annular sealing groove, and a circumferential sealing strip is embedded in the annular sealing groove;
- a percolation medium channel and a sealing medium injection channel are arranged in the indenter body, one end of the sealing medium injection channel is communicated with the annular sealing groove, and the other end of the sealing medium injection channel passes through an outer surface of the indenter body; and
- a front end face of the rectangular convex block is provided with an integrally-manufactured embedding groove, the permeation block is embedded in the embedding groove, a plurality of permeation holes are uniformly distributed in the permeation block, the permeation holes are communicated with the permeation block from front to back, one end of the percolation medium channel is communicated with the embedding groove, and the other end of the percolation medium channel is communicated with the outer surface of the indenter body.

6. The rock physico-mechanical testing and three-dimensional multi-field information perception cabin in simulated environments of deep earth, deep space, and deep sea according to claim 5, further comprising: a sample holder, wherein the sample holder comprises a rigid outer cubic frame and a flexible inner cubic frame, the rigid outer cubic frame and the flexible inner cubic frame are both provided with 12 frame edges, 6 faces of the rigid outer cubic frame and 6 faces of the flexible inner cubic frame are both rectangular frames, and 12 outside corner positions of the flexible inner cubic frame are attached to 12 inside corners of the rigid outer cubic frame;
- each face of the flexible inner cubic frame is provided with an integrally-manufactured annular flange, wherein the annular flange is adapted to an annular groove of the circumferential sealing strip; and
- the sample may be loaded in the flexible inner cubic frame, 6 indenters respectively pass through frame openings of the rigid outer cubic frame and the flexible inner cubic frame in 6 directions, and annular flanges on 6 faces of the flexible inner cubic frame are correspondingly loaded in annular grooves of circumferential sealing strips of the 6 indenters.

7. The rock physico-mechanical testing and three-dimensional multi-field information perception cabin in simulated environments of deep earth, deep space, and deep sea according to claim 4, wherein 12 elastic pieces are used to connect 6 indenters together, and a periphery of each indenter is connected to 4 indenters on the periphery through one elastic piece.

* * * * *